United States Patent [19]
Ono et al.

[11] Patent Number: 5,522,915
[45] Date of Patent: Jun. 4, 1996

[54] METHOD AND APPARATUS FOR SEQUENTIALLY AND CONTINUOUSLY DETERMINING CONCENTRATIONS OF CARBON, HYDROGEN, AND NITROGEN IN MOLTEN STEEL, AND METHOD AND APPARATUS FOR RAPIDLY DETERMINING TRACE AMOUNTS OF CARBON IN MOLTEN STEEL

[75] Inventors: Akihiro Ono, Kawasaki; Masaki Ina, Tokai; Hiroaki Kosaka; Toshihiro Ogura, both of Osaka, all of Japan

[73] Assignee: Heraeus Electronite Japan, Ltd., Osaka, Japan

[21] Appl. No.: 300,722

[22] Filed: Sep. 2, 1994

[30] Foreign Application Priority Data

Sep. 3, 1993 [JP] Japan .................................. 5-220137
Sep. 3, 1993 [JP] Japan .................................. 5-220138

[51] Int. Cl.$^6$ .................................................. C21C 1/04
[52] U.S. Cl. ....................... 75/385; 75/375; 266/80; 266/90; 266/99
[58] Field of Search ................... 266/80, 79, 90, 266/99; 75/375, 376, 377, 384, 385, 386

[56] References Cited

U.S. PATENT DOCUMENTS 3,816,720  6/1974  Bauer et al. ............................ 75/384
4,055,212  10/1977  Vogel ........................................ 75/384
5,226,950  7/1993  Yu ............................................. 266/80

FOREIGN PATENT DOCUMENTS 2247327  10/1990  Japan ........................................ 75/385

Primary Examiner—Scott Kastler
Attorney, Agent, or Firm—Armstrong, Westerman, Hattori, McLeland & Naughton

[57] ABSTRACT

Disclosed herein is a method of sequentially and continuously determining the concentrations of carbon, hydrogen, and nitrogen in molten steel using a single apparatus. Disclosed also herein are a method and an apparatus for determining trace amounts of carbon in molten steel which are the specialized application of the principle used for the above-mentioned method.

Said method comprises bubbling through molten steel a carrier gas selected according to any specific element to be determined in molten steel, recovering the carrier gas containing the specific element, circulating or passing the recovered carrier gas through a gas circulating circuit so that the concentration of the specific element in the carrier gas reaches an approximate or complete equilibrium with the concentration of the specific element in molten steel, determining the concentration of the specific element by the means to determine the concentration of one or more specific elements, (and in the case of determination of several elements) discharging the carrier gas from the gas circulating circuit and repeating said steps with a renewed carrier gas to determine the remaining elements to be determined.

6 Claims, 15 Drawing Sheets

METHOD AND APPARATUS FOR SEQUENTIALLY AND CONTINUOUSLY DETERMINING CONCENTRATIONS OF CARBON, HYDROGEN, AND NITROGEN IN MOLTEN STEEL, AND METHOD AND APPARATUS FOR RAPIDLY DETERMINING TRACE AMOUNTS OF CARBON IN MOLTEN STEEL

BACKGROUND OF THE INVENTION

1. Field of the Invention

The first aspect of the present invention relates to a method and apparatus for sequentially and continuously determining the concentrations of carbon, hydrogen, and nitrogen in molten steel.

The second aspect of the present invention relates to a method and apparatus for rapidly determining trace amounts of carbon in molten steel with no deoxidation or slight deoxidation. The method and apparatus in the second aspect are basically the same as those in the first aspect. More particularly, the second aspect of the present invention relates to a method and apparatus for rapidly and accurately determining trace amounts of carbon which could not be determined directly by the conventional method. The method and apparatus can be effectively used when dissolved carbon is removed from molten steel with no deoxidation or slight deoxidation using a vacuum decarburizing unit such as RH degassing unit.

2. Description of the Prior Art

It is of the utmost importance in a steel mill to control the concentrations of carbon, hydrogen, and nitrogen in molten steel. In fact, it is necessary to control the concentrations of either nitrogen and hydrogen or either nitrogen and carbon, depending on the refinery involved. Of these three elements, carbon has recently become a matter of great concern. Especially, the determination of carbon concentrations in ultralow carbon steel sheet is attracting considerable attention. The reason for this is explained below.

Ultralow carbon steel sheet has been widely in use mainly for automobiles. As compared with low carbon steel, it is superior in ductility and deep-drawability. On the other hand, it suffers a disadvantage of lacking sufficient mechanical strength. Therefore, many attempts have been made to improve its mechanical strength while maintaining its ductility. This object is achieved by, for example, adding any one or two of such elements as Ti, Nb, Mn, and P. Another important factor to be considered is to control trace amounts of carbon. If it is possible to control trace amounts of carbon, it would be possible to reduce the kinds and amount of additives. For this reason, there is a demand in the steel making industry for a technique to control the concentration of trace amounts of carbon to a precision of the order of ppm in molten steel containing 10–100 ppm of carbon.

The process for producing ultralow carbon steel in a steel mill involves the use of a vacuum decarburizing unit (typified by RH degassing unit). According to this process, decarburization is accomplished by the reaction in vacuo of dissolved carbon in molten steel (with no deoxidation or slight deoxidation) and dissolved oxygen to give carbon monoxide. This is the background to be taken into account in establishing the method of determining trace amounts of carbon in molten steel.

There are some methods for rapid determination of carbon concentration in molten steel. They include freezing point measurement and emission spectrophotometry. Unfortunately, they are not suitable for rapid determination of low carbon concentrations.

A technique is being used on trial to estimate the carbon concentration in the RH degassing unit. According to this technique, CO and $CO_2$ are sampled from the gas sucked under vacuum from the molten steel and the sample gas is analyzed by means of a mass spectrometer. The cumulative amount of CO and $CO_2$ indicates the amount of carbon removed. A disadvantage of this technique is that sampling from the vacuum system is difficult to carry out and calculations are subject to errors because the total amount of gas evolved is not known exactly. In addition, leakage from the vacuum vessel presents difficulties in accurately estimating the carbon concentration in molten steel. The lower the carbon concentration in molten steel, the greater the difficulty. No procedure has been established yet to rapidly determine the concentration of trace amounts of carbon.

Although there have been proposed several methods for rapidly determining carbon concentrations, none of them are satisfactory.

In addition to a demand for a method of rapidly determining the concentration of trace amounts of carbon, there is also a demand for an apparatus for continuously determining the concentrations of other elements (such as hydrogen and nitrogen) than carbon contained in molten steel. There may be no instance where it is necessary to determine these three elements simultaneously; however, there does exist an instance in a steel mill where it is necessary to continuously determine two elements, namely nitrogen and carbon or nitrogen and hydrogen.

There is a pioneering technique relating to the determination of several elements, namely carbon, hydrogen, and nitrogen. It is disclosed in Japanese Patent Kohyo No. 502776/1989. It is chiefly intended to determine batchwise the hydrogen concentration. Its procedure consists of blowing a carrier gas (an inert gas) into molten steel for bubbling, recovering the gas, and determining hydrogen in the recovered gas. The results of determination indicate the hydrogen concentration in molten steel. The disclosure suggests that the same procedure can also be applied to the batchwise determination of carbon monoxide and nitrogen in the recovered gas.

The apparatus for this procedure is schematically shown in FIG. 16. It is composed of a probe (150), with its lower part placed in molten steel under examination for gas bubbling and gas collection, and a gas circulating circuit (151), which is made up of a carrier gas supplier and a gas analyzer. The probe (150) is made up of a gas blowing tube (100), with its lower part bent into a U-shape, and a gas collecting tube (101), with its open end positioned above the U-shape. Above the opening of the gas blowing tube (100) is a bell-shaped part (102) of porous material to collect the carrier gas efficiently while preventing the molten steel from entering the gas collecting tube (101).

The gas circulating circuit (151) is made up of a filter (103), thermal conductivity detector (104), pump (105), four-way stopcock (106), pressure gauge (107), and flow meter (108), which are arranged along the gas flow.

The apparatus is operated in the following manner to determine the hydrogen concentration. A carrier gas supplied from a gas cylinder (109) is allowed to bubble in molten steel through the gas blowing tube (100). The carrier gas mixed with dissolved hydrogen in molten steel is collected by the gas collecting tube (101). The collected carrier gas is allowed to circulate through the gas circulating circuit (151) so that the hydrogen concentration in the gas is equilibrated with the hydrogen concentration in the molten steel. Finally, the hydrogen concentration is determined by means of the thermal conductivity detector (104).

If the above-mentioned technique is to be used to determine the concentrations of carbon, hydrogen, and nitrogen, it is necessary to replace the single thermal conductivity detector (104) by a plurality of thermal conductivity detectors arranged in series, each (except the first one) preceded by a filter to remove unwanted gas components. The first thermal conductivity detector measures the total pressures of carbon monoxide, hydrogen, nitrogen, and carrier gas. The second thermal conductivity detector preceded by a hydrogen filter measures the total pressures of carbon monoxide, nitrogen, and carrier gas. The third thermal conductivity detector preceded by a carbon monoxide filter measures the total pressures of nitrogen and carrier gas. The final thermal conductivity detector preceded by a nitrogen filter measures the total pressure of carrier gas alone. Thus, it is possible to obtain the respective partial pressures of carbon monoxide, hydrogen, and nitrogen from the difference in total pressure between the adjacent two stages.

The above-mentioned disclosure suggests the continuous determination of carbon monoxide, hydrogen, and nitrogen; however, it mentions nothing about a concrete means to determine carbon. The complete lack of disclosure about the rapid determination of trace amounts of carbon in molten steel frustrates those who need it in a steel mill.

In addition, the above-mentioned apparatus is designed such that the carrier gas, which after recovery from molten steel contains carbon monoxide, hydrogen, and nitrogen is circulated through the gas circulating circuit, during which these gases are filtered and determined sequentially. This method, however, is impracticable in principle.

The above-mentioned apparatus is useful only when molten steel contains dissolved hydrogen and nitrogen (to be determined) in the form of atoms displaying certain partial pressures in equilibrium at a given temperature and pressure. It is totally unapplicable to the determination of carbon. Carbon in itself present in molten steel does not possess its intrinsic partial pressure at the ordinary refining temperature. Therefore, it is impossible to sample carbon in the form of gas mixed with the carrier gas.

The investigation into the composition of the carrier gas recovered from molten steel revealed that it impossible that hydrogen and carbon monoxide exist simultaneously in the carrier gas. It follows that molten steel containing oxygen in low concentrations gives off no carbon monoxide and conversely molten steel containing oxygen in high concentrations gives off no hydrogen. It was found by the investigation that molten steel gives off hydrogen when its oxygen content is low as in the case of killed steel. This suggests that dissolved hydrogen reacts with oxygen to give water (in the form of steam) when molten steel contains oxygen in high concentrations. It was also found by the investigation that molten steel gives off carbon monoxide when its oxygen content is higher than 200 ppm (as in the case of steel with no deoxidation or slight deoxidation). This suggests that dissolved carbon reacts with oxygen to give carbon monoxide. It follows that molten steel containing oxygen in low concentrations gives off no carbon monoxide because of too small quantities of oxygen available for reaction. It turned out that carbon monoxide is formed by the same reaction as that involved in decarburization by a vacuum refinery. It is apparent from the foregoing that the technology disclosed in the abovementioned Japanese patent cannot be applied to the determination of trace amounts of carbon in molten steel with no deoxidation or slight deoxidation which is the object of the present invention.

Moreover, the above-mentioned prior art technology has a shortcoming in continuously determining hydrogen and carbon monoxide using the carrier gas common to them. That is, if hydrogen enters the carrier gas in the presence of dense oxygen, it reacts with oxygen in the carrier gas to give water, making it impossible to determine the concentration of hydrogen, which is the prime object. To avoid this, it is necessary to determine the concentration of hydrogen in the presence of rarefied oxygen. By contrast, it is necessary to determine the concentration of carbon monoxide in the presence of dense oxygen because carbon monoxide does not form in the presence of rarefied oxygen.

As mentioned above, the prerequisite conditions for the determination of hydrogen concentration differ from those for the determination of carbon concentration. Therefore, it is unjustifiable to use the carrier gas recovered from molten steel for determination of both hydrogen concentration and carbon concentration.

In the case where the concentration of a specific element is to be determined by a thermal conductivity detector, it is desirable for accurate determination that there be as great a difference as possible in thermal conductivities between the element and the carrier gas. Unfortunately, there is a large difference in thermal conductivities between hydrogen and nitrogen and hence it is difficult to use a single carrier gas for determination of both hydrogen concentration and nitrogen concentration. Some device is necessary to overcome this difficulty.

Since the technique disclosed in the above-mentioned Japanese Patent Kohyo No. 502776/1989 cannot be used as such for the continuous determination of carbon, hydrogen, and nitrogen, it is common practice to install several analyzers, each designed to determine the concentration of one element only, in order to determine the concentrations of several elements in a steel mill. Operation of several analyzers needs a lot of time and trouble, which prevents the results of determination from being used effectively for feedback control.

SUMMARY OF THE INVENTION

The first aspect of the present invention was completed in view of the foregoing. Accordingly, it is an object of the first aspect of the present invention to provide a method and apparatus for determining the concentration of carbon, hydrogen, and nitrogen in molten steel sequentially and continuously using a single apparatus.

It is an object of the second aspect of the present invention to provide a method and apparatus for determining accurately and rapidly the concentration of trace amounts of carbon which could not be determined directly by the conventional method.

DETAILED DESCRIPTION OF THE INVENTION

Figure 1:
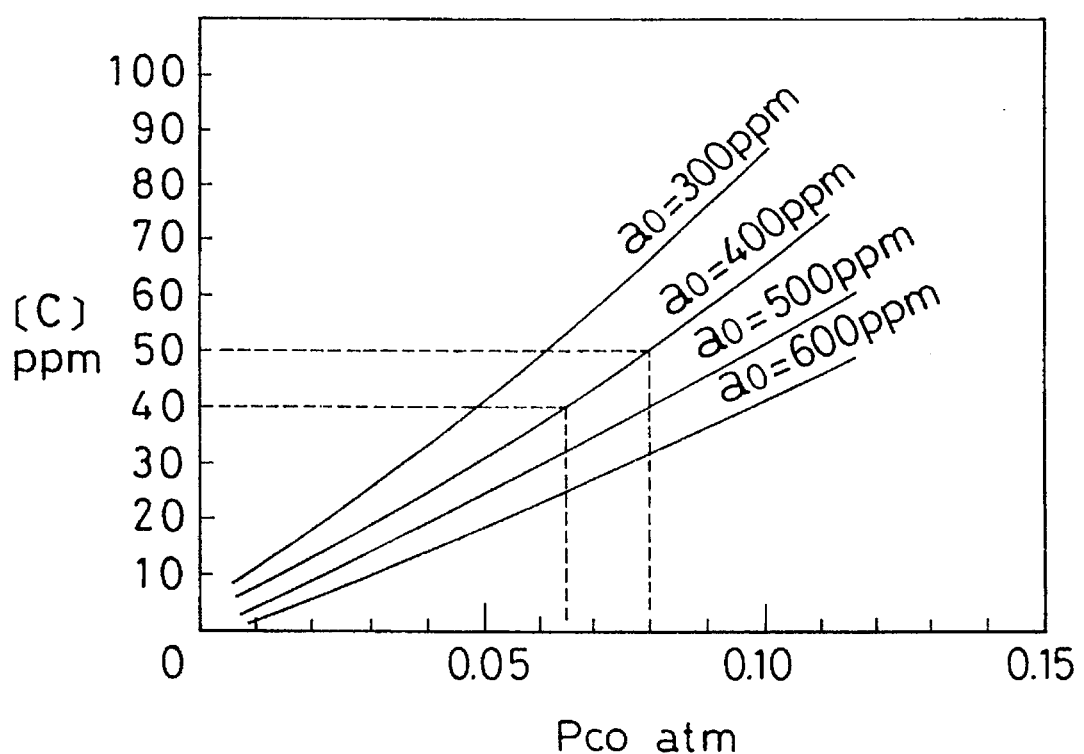
FIG. 1 is a graph showing the relationship between carbon monoxide and carbon in molten steel.

After extensive researches, the present inventors struck on an idea that the object is achieved by slight modification of the gas probe and gas circulation circuit disclosed in the above-mentioned Japanese Patent as long as the determination of hydrogen and nitrogen in molten steel is concerned. The problem is how to determine trace amounts of carbon in molten steel.

It would be possible to estimate the concentration of carbon in molten steel by analyzing carbon monoxide emitted from molten steel if some means is found which promotes the formation of carbon monoxide. This idea is based on the fact that when molten steel containing trace amounts of carbon and oxygen is placed in a vacuum or an environment with a low concentration of carbon monoxide, carbon monoxide in trace amounts is formed and released from the molten steel, with the equilibrium concentration of carbon monoxide being associated with the concentration of carbon as well as oxygen in molten steel. To be able to estimate the carbon concentration, it is necessary that the concentration of oxygen in molten steel is known or its change is predictable. However, it would be safe to assume that in the case of such refining unit as RH degassing unit, in which the oxygen concentration in molten steel is high and stable at hundreds of ppm, the concentration of carbon monoxide in the gas from molten steel depends solely on the concentration of carbon in molten steel.

The object of causing carbon monoxide to be formed in and released from molten steel efficiently would be achieved by blowing a carrier gas into molten steel in the same manner as used in the above-mentioned hydrogen analyzer. In other words, the reaction of trace amounts of carbon with oxygen in molten steel would be promoted by bubbling a carrier gas (free from carbon monoxide) in molten steel so that bubbles stir molten steel and provide large and fresh reaction surfaces in molten steel. Incidentally, since bubbling gives rise to not only carbon monoxide but also extremely small quantities of carbon dioxide (which will be collectively referred to as carbon oxides hereinafter), it is necessary to determine both of them for accurate determination of carbon.

The above-mentioned concepts led to the present invention relating to a method of determining sequentially and continuously carbon, hydrogen, and nitrogen in molten steel.

The method of the present invention comprises bubbling through molten steel a carrier gas (or inert gas) selected according to any specific element to be determined among carbon, hydrogen, and nitrogen in molten steel, recovering the carrier gas containing the specific element through the gas supply-recover probe immersed in molten steel, circulating or passing the recovered carrier gas through a gas circulating circuit, performing the bubbling and recovery of the carrier gas once or several times so that the concentration of the specific element in the carrier gas reaches an approximate or complete equilibrium with the concentration of the specific element in molten steel, determining the concentration of the specific element by the means to determine the concentration of one or more specific elements which is installed in said gas circulating circuit or in the gas circuit branching off from said gas circulating circuit, discharging the carrier gas from the gas circulating circuit to complete a series of steps for determining the concentration of the specific element, and repeating said steps with a renewed carrier gas to determine the remaining elements to be determined.

The method of the present invention consists basically of selecting a proper carrier gas according to any one of carbon, hydrogen, and nitrogen to be determined, and discharging the used carrier gas from the gas circulating circuit each time after determination of a specific element. However, it is possible to use the same carrier gas for the determination of carbon, hydrogen, and nitrogen, if the carrier gas is properly selected.

An embodiment of the present invention comprises at least two of three steps of determining the hydrogen concentration, determining the carbon concentration, and determining the nitrogen concentration, which are described below.

The step of determining the hydrogen concentration consists of blowing a carrier gas (composed mainly of helium or argon) for bubbling into molten steel, thereby stirring molten steel and causing hydrogen in molten steel to diffuse into the carrier gas, recovering the carrier gas through a probe (for gas supply and recovery) immersed in molten steel, circulating or passing the recovered carrier gas through a gas circulating circuit, repeating the blowing and recovery of the carrier gas if necessary so that the hydrogen concentration in the carrier gas increases gradually until it equilibrates with the hydrogen concentration in molten steel, repeating the circulation of the carrier gas as many times as required or for a prescribed period of time, determining the hydrogen concentration in the equilibrated carrier gas using a hydrogen analyzer provided in the gas circulating circuit or a branch circuit diverting from the gas circulating circuit, and finally discharging the carrier gas from the gas circulating circuit.

The step of determining the carbon concentration consists of blowing a carrier gas (composed mainly of helium or argon) for bubbling into molten steel, thereby stirring molten steel and causing carbon to react with oxygen at interface between molten steel and bubbles to give carbon monoxide and carbon dioxide in the carrier gas, recovering the carrier gas (containing carbon oxides) through a probe (for gas supply and recovery) immersed in molten steel, circulating or passing the recovered carrier gas through a gas circulating circuit provided with a carbon oxides analyzer, repeating the blowing and recovery of the carrier gas if necessary so that the carbon oxides concentration in the carrier gas increases gradually until it equilibrates with the carbon and oxygen concentrations in molten steel, repeating the circulation of the carrier gas as many times as required or for a prescribed period of time, determining the concentrations of carbon oxides in the equilibrated carrier gas using the carbon oxides analyzer, and estimating the carbon concentration in molten steel from the relationship between the carbon oxides concentration and the oxygen concentration in molten steel (which is determined separately from this determination or at the same as this determination).

The step of determining the nitrogen concentration consists of blowing a carrier gas (composed mainly of helium or argon) for bubbling into molten steel, thereby stirring molten steel and causing nitrogen in molten steel to diffuse into the carrier gas, recovering the carrier gas through a probe (for gas supply and recovery) immersed in molten steel, circulating or passing the recovered carrier gas through a gas circulating circuit provided with a nitrogen analyzer, repeating the blowing and recovery of the carrier gas if necessary so that the nitrogen concentration in the carrier gas increases gradually until it equilibrates with the nitrogen concentration in molten steel, repeating the circulation of the carrier gas as many times as required or for a prescribed period of time, and determining the nitrogen concentration in the equilibrated carrier gas using the nitrogen analyzer.

This embodiment is characterized in that the probe for gas supply and recover and the gas circulating circuit are used for the determination of hydrogen, carbon, and nitrogen in common.

It will take a long time before an equilibrium is reached because nitrogen is slower in diffusion than carbon monoxide and hydrogen. In order to expedite the determination, it is desirable to predict the average equilibrium value of nitrogen concentration from the rising curve of the nitrogen concentration obtained in the initial stage of determination and to add nitrogen compulsorily from a nitrogen cylinder according to the predicted value so as to establish an equilibrium as soon as possible.

The above-mentioned method is put to practice by an apparatus for determining sequentially and continuously the concentrations of carbon, hydrogen, and nitrogen in molten steel, said apparatus comprising one or more than one source to supply an inert gas as a carrier gas according to the element to be determined; a gas supply-recover probe consisting of a gas blowing tube with an open end and a gas recovery tube to recover the carrier gas through a porous part which is positioned in molten steel above the open end of the gas blowing tube; a gas circulating circuit through which the carrier gas supplied from the carrier gas source is circulated compulsorily by a circulating pump through the gas supply-recover probe as many times as required or for a prescribed period of time; a group of means to determine the concentration of a specific element (such as the means to determine the concentration of carbon oxides, the means to determine the concentration of hydrogen, and the means to determine the concentration of nitrogen) installed in the gas circulating circuit or in a gas circuit branching off from the gas circulating circuit; a means to determine the concentrations of oxygen which is constructed integrally with or separately from the gas supply-recover probe; and an arithmetic unit which receives the data of the concentrations of carbon oxides and oxygen from the means to determine the concentrations of carbon oxides and oxygen and calculates the concentration of carbon in molten steel from such data.

In the case where determination is carried out in a refinery where the concentration of oxygen is known or predictable, it is not necessary to install the means to determine the concentration of oxygen.

It is desirable that the means to determine the concentrations of specific elements be provided with a means to preliminarily purify the carrier gas of harmful components which might cause errors in determination.

The means to determine the concentrations of specific elements may be available in various types. It is desirable to use an infrared gas analyzer as a means to determine the concentration of carbon oxides, to use a semiconductor gas sensor as a means to determine the concentration of hydrogen, and to use a thermal conductivity detector to determine the concentration of nitrogen.

The following is the procedure for operating the apparatus of the present invention for determining sequentially and continuously the concentrations of carbon, hydrogen, and nitrogen in molten steel. First, a carrier gas (selected according to the gas to be determined) is supplied from the gas supply source. The carrier gas is blown into molten steel through the gas blowing tube of the gas supply-recover probe. The blown carrier gas is allowed to bubble in molten steel. The bubbling stirs molten steel and causes the element to be determined in molten steel to diffuse into the carrier gas. The carrier gas is recovered through the gas recovery tube of the gas supply-recover probe. Not only does the bubbling permit dissolved hydrogen and nitrogen in molten steel to be collected together with the carrier gas, but it also promotes the reaction between carbon and oxygen at the interface between molten steel and bubbles, thereby forming carbon monoxide. This carbon monoxide is also recovered together with the carrier gas. This carbon monoxide is accompanied by trace amounts of carbon dioxide, which is also recovered together with the carrier gas.

The rising carrier gas is recovered by the gas recovery tube through the porous part and then circulated through the gas circulating circuit as many times as required and for a prescribed period of time until an equilibrium is reached. The concentration of a specific element in the carrier gas is determined by the means (to determine the concentration of specific elements) installed in the gas circulating circuit. There may be an instance in which the carrier gas is circulated only once through the gas circulating circuit.

Different carrier gases are used according to the elements (carbon, hydrogen, and nitrogen) to be determined. Each time the determination of an element is completed, the carrier gas is discharged from the gas circulating circuit, and a new carrier gas is used for the subsequent operations.

The concentrations of hydrogen and nitrogen are determined directly by the means to determine the concentration of hydrogen and the means to determine the concentration of nitrogen which are installed in the gas circuit or a gas circulating circuit branching off from the gas circulating circuit. However, the concentration of carbon is determined indirectly. That is, the concentrations of carbon monoxide and carbon dioxide (collectively referred to as the concentration of carbon oxides) in the carrier gas is determined first by the means installed in the gas circulating circuit. Then, the result of determination is compared by computation with the concentration of oxygen which has been determined separately. In this way the concentration of carbon oxides is estimated. Incidentally, in the case where the concentration of oxygen is close to saturation or known or predictable (and hence the concentration of oxygen is regarded as constant), it is possible to estimate unequivocally the concentration of carbon on the basis only on the concentration of carbon oxides.

In determination of hydrogen concentrations, an equilibrium is reached soon; however, in determination of carbon and nitrogen concentrations, it will take a considerable time before an equilibrium is reached. Therefore, in the latter case, it is common practice to estimate the concentrations before an equilibrium is reached. For example, in determination of carbon concentration, the concentration of carbon oxides is determined after a certain number (or time) of cycles of circulation before an equilibrium is reached between the concentration of carbon oxides in molten steel and the concentration of carbon oxides in the carrier gas. This practice is practicable if a relationship is established between the concentration of carbon in molten steel and the concentration of carbon oxides in the carrier gas after a certain number (or time) of cycles of circulation. Therefore, it leads to rapid determination and permits the results of determination to be used for feedback control in the refinery.

Since nitrogen is slow in diffusion, it is common practice in determination of nitrogen concentration to predict the average equilibrium value of nitrogen concentration from the rising curve of the nitrogen concentration obtained in the initial stage of determination and to add nitrogen compulsorily from a nitrogen cylinder according to the predicted value so as to establish an equilibrium as soon as possible.

Based on the above-mentioned idea, the rapid determination of trace amounts of carbon in molten steel is accomplished in the following manner by the bubbling of a carrier gas and the recovery of the bubbled carrier gas.

The procedure consists of bubbling a carrier gas (an inert gas) through molten steel, thereby stirring molten steel and causing carbon and oxygen to react with each other at the interface between bubbles and molten steel to give carbon monoxide and carbon dioxide, recovering the carrier gas together with carbon monoxide and carbon dioxide, circulating or passing the recovered carrier gas through the gas circuit in which is installed a means to determine the concentration of carbon oxides, performing the steps of the bubbling and recovery of the carrier gas once or several times, thereby gradually increasing the concentrations of carbon monoxide and carbon dioxide in the carrier gas until they equilibrate with those of oxygen and carbon in molten steel, determining the concentrations of carbon monoxide and carbon dioxide in the carrier gas by the above-mentioned means to determine the concentrations of carbon oxides after the circulation has been carried out as many times as required or for a prescribed period of time, and estimating the concentration of carbon in molten steel from the relationship between the concentrations of carbon monoxide and carbon dioxide and the concentration of oxygen in molten steel.

In the case where determination is carried out in a refinery where the oxygen concentration is known or predictable, it is not necessary to determine the oxygen concentration but it is possible to unequivocally specify the concentration of carbon in molten steel on the basis of the concentration of carbon oxides which is determined assuming that the oxygen concentration is constant.

The above-mentioned method for rapidly determining trace amounts of carbon in molten steel is embodied by an apparatus which comprises a source to supply an inert gas as a carrier gas; a gas supply-recover probe consisting of a gas blowing tube with an open end and a gas recovery tube to recover the carrier gas through a porous part which is positioned in molten steel above the open end of the gas blowing tube; a gas circulating circuit through which the carrier gas supplied from the carrier gas source is circulated compulsorily by a circulating pump through the gas supply-recover probe as many times as required or for a prescribed period of time, said gas circulating circuit being provided therein a means to determine the concentrations of carbon oxides; a means to determine the concentrations of oxygen which is constructed integrally with or separately from the gas supply-recover probe; and an arithmetic unit which receives the data of the concentrations of carbon oxides and oxygen from the means to determine the concentrations of carbon oxides and oxygen and calculates the concentration of carbon in molten steel from such data.

In the case where determination is carried out in a refinery where the oxygen concentration is known or predictable, it is not necessary to install the means to determine the oxygen concentration.

The apparatus for rapidly determining trace amounts of carbon in molten steel is operated in the following manner. First, the carrier gas supplied from the gas supply source is blown into molten steel through the gas blowing tube. The blown carrier gas stirs molten steel and promotes reaction between carbon and oxygen in molten steel to give carbon monoxide and carbon dioxide. The carbon monoxide and carbon dioxide rise to the surface together with the carrier gas. The carrier gas is recovered by the gas recovery tube through the porous part. The recovered carrier gas is circulated through the gas circulating circuit as many times as required or for a prescribed period of time. The concentration of carbon monoxide and carbon dioxide (collectively referred to as carbon oxides hereinafter) in the carrier gas is determined by the means (to determine the concentration of carbon oxides) installed in the gas circulating circuit. The results of determination are processed by an arithmetic unit together with the concentration of oxygen determined by the means to determine the concentration of oxygen. In this way it is possible to specify the concentration of carbon in molten steel. Incidentally, there may be an instance in which the carrier gas is circulated only once through the gas circulating circuit. It is desirable that the determination of carbon oxides be carried out after an equilibrium has been reached between the concentration of carbon oxides in molten steel and the concentration of carbon oxides in the carrier gas collected. However, if it is necessary to shorten the time for determination, it is possible to determine the concentration of carbon oxides when the circulation through the gas circulation circuits has been repeated as many times as required or for a prescribed period of time. This practice is practicable if a relationship is established between the concentration of carbon in molten steel and the concentration of carbon oxides in the carrier gas after a certain number (or time) of cycles of circulation. Therefore, it leads to rapid determination, without necessity of waiting for an equilibrium to come, and permits the results of determination to be used for feedback control in the refinery.

EXAMPLES

The invention will be described in more detail with reference to the following examples which are illustrated in the accompanying drawings.

FIG. 1 is a known graph showing the relationship between the partial pressure of carbon monoxide ($P_{CO}$) in molten steel and the concentration of carbon in molten steel. The four curves shown represent respectively the relationship between the partial pressure (or concentration) of carbon monoxide and the concentration of carbon in the case where the oxygen activity ($a_O$) is 300 ppm, 400 ppm, 500 ppm, and 600 ppm. It is apparent from this graph that it is possible to estimate unequivocally the concentration of carbon in molten steel by determining the concentration of carbon monoxide in the gas phase if the value of oxygen activity (or oxygen concentration) is known. It is also noted from the graph that it is possible to determine the concentration of trace amounts of carbon in the range of 10–100 ppm by determining the concentration of carbon monoxide in the range of 1–15%. In other words, it is possible to accurately estimate the concentration of carbon of the order of ppm by determining the concentration of carbon monoxide of the order of percent. The present invention is based on this principle to determine the concentration of carbon in molten steel.

Figure 2:
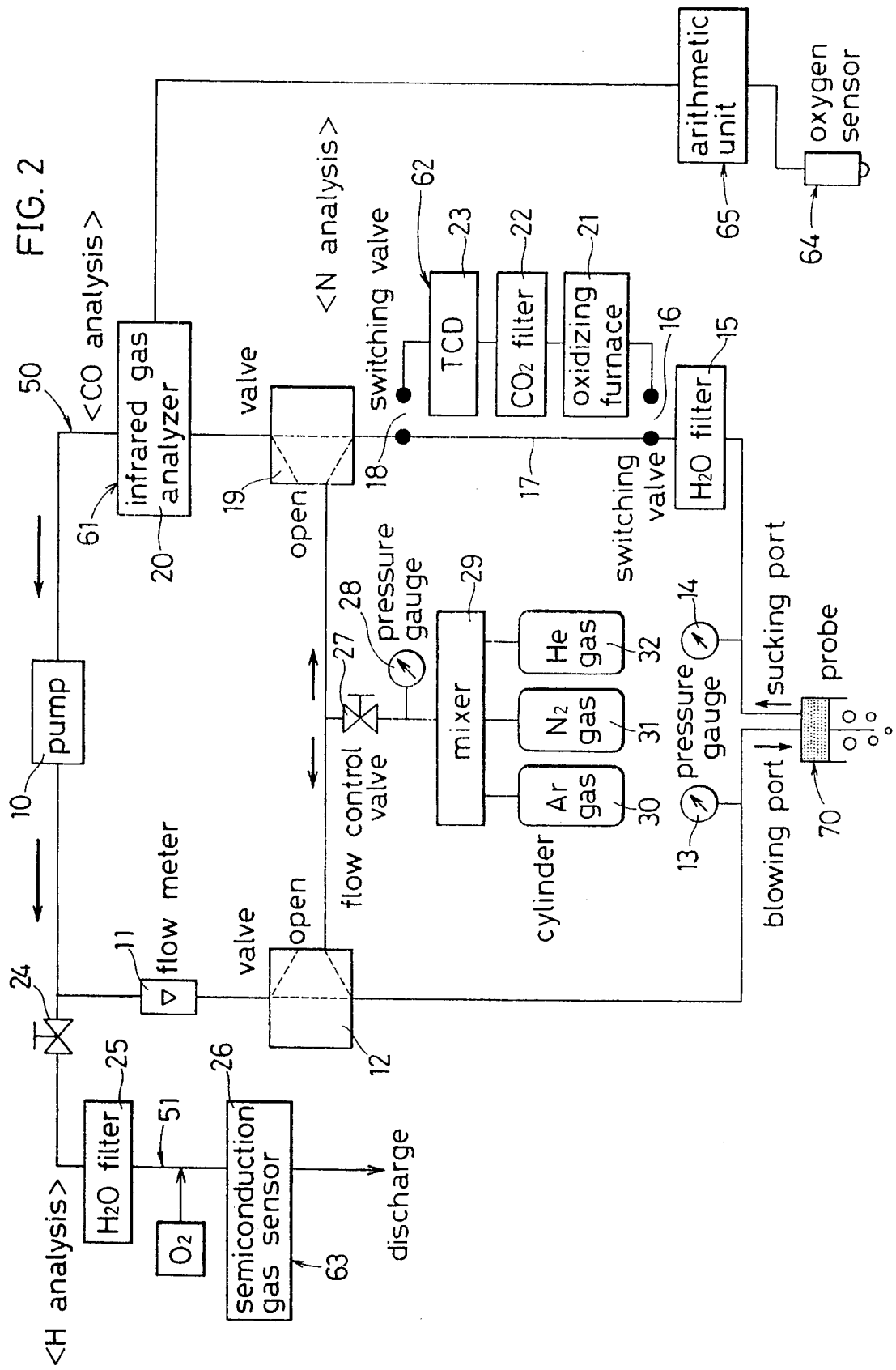
FIG. 2 is a schematic illustration of an embodiment of the apparatus for continuous and sequential determination pertaining to the present invention.
Figure 3:
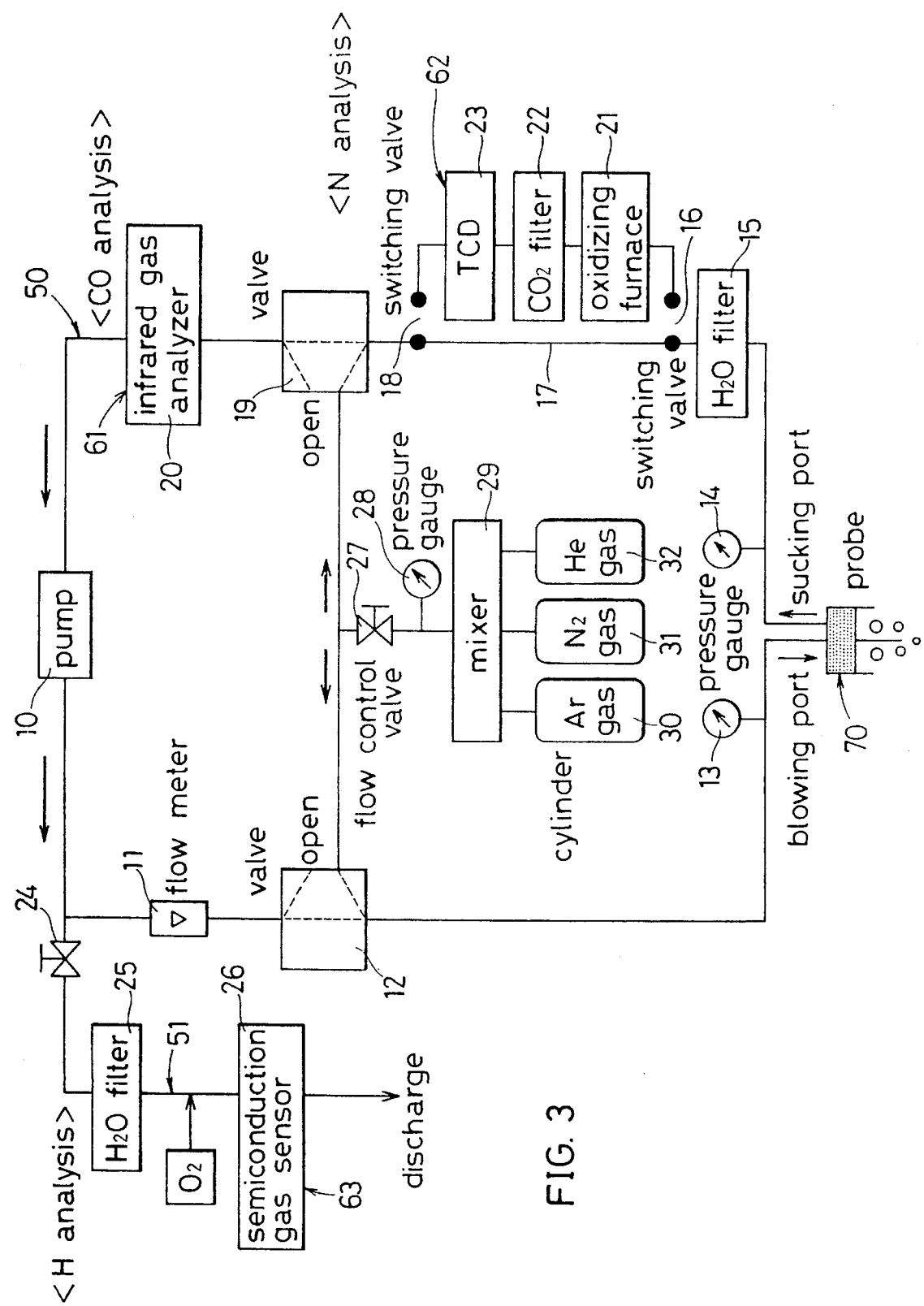
FIG. 3 is a schematic illustration of another embodiment of the apparatus for continuous and sequential determination pertaining to the present invention.

FIG. 2 is a schematic representation of an embodiment of the apparatus of the present invention for sequential and continuous determination. This apparatus is made up mainly of the gas circulating circuit (50) in which are installed the unit for determining the concentration of carbon oxides (61) and the unit for determining the concentration of nitrogen (62), the gas branch circuit (51) in which is installed the unit for determining the concentration of hydrogen (63), the gas supply-recover probe (70) exchangeably connected to the gas circulating circuit (50) by a connector (not shown), the unit for determining the concentration of oxygen (64) which is independent of the gas circulating circuit (50), and the arithmetic unit (65) to calculate the concentration of carbon in molten steel from the values obtained by the unit for determining the concentration of carbon oxides (61) and the unit for determining the concentration of oxygen (64). In the case where the concentration of oxygen is high and stable in the equipment as typified by the RH degassing equipment, it is possible to assume that the concentration of oxygen is constant. In this case, it is possible to remove the unit for determining the concentration of oxygen (64), as shown in FIG. 3. In the drawings which are referred to in the following description, the unit for determining the concentration of oxygen (64) is not shown intentionally. However, it may be installed if necessary.

Figure 4:
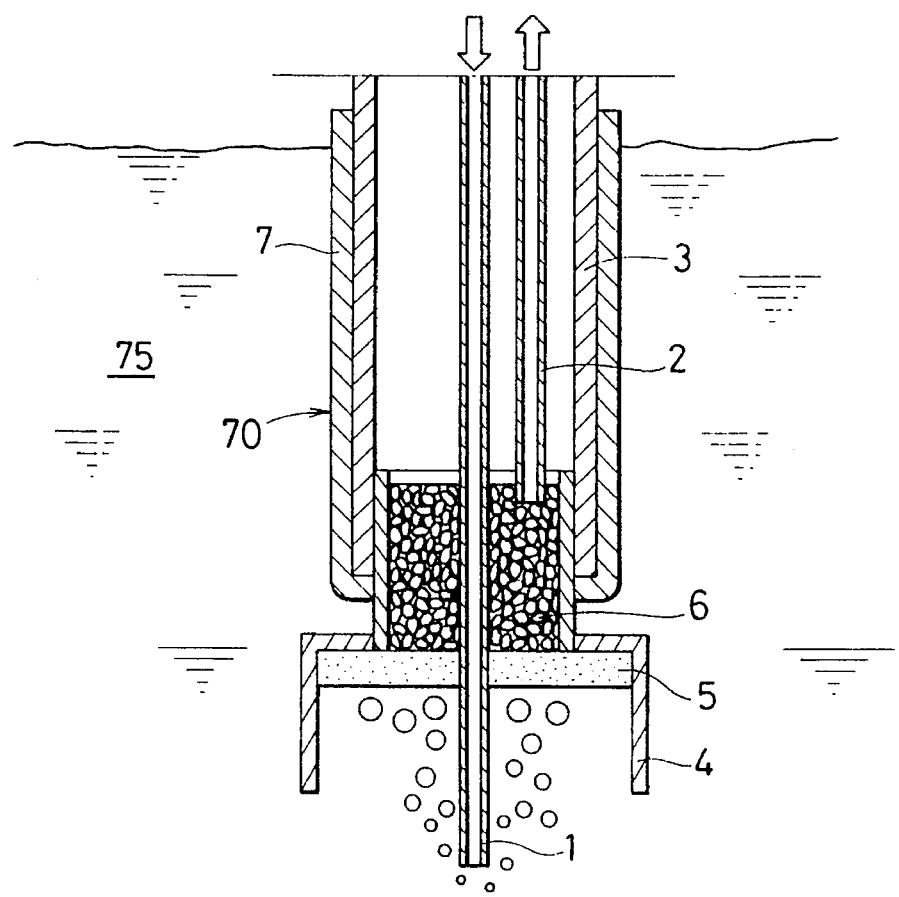
FIG. 4 is a sectional view of an embodiment of the gas supply-recover probe.

The gas supply-recover probe (70) is shown in FIG. 4. It is composed of the gas blowing tube (1) with an open end and the gas recovery tube (2). The two tubes are passed through and held in the holder (3) such as a cardboard cylinder. The open end of the gas recovery tube (2) is positioned above the open end of the gas blowing tube (1). To the lower end of the holder (3) is attached the skirt (4) for gas collection. The skirt (4) is made of a stable material such as quartz, which will not melt and release any component to cause errors when it is immersed in molten steel during determination. The gas blowing tube (1) or at least that part thereof which is immersed in molten steel is made of a refractory such as zirconia so that it will not melt and release unnecessary components when it is immersed in molten steel. The holder (3) is coated with a refractory (7) for protection from the heat of molten steel. It is desirable that the open end of the gas blowing tube (1) be plugged with a low-melting material which is melted by the heat of molten steel so that the plugged end is opened automatically when the gas blowing tube (1) is immersed to a prescribed depth in molten steel.

The skirt (4) has its bottom of opening filled with a porous refractory (5) such as porous alumina. The porous refractory (5) passes the carrier gas released from molten steel but blocks molten steel. The skirt (4) is connected to a part of smaller diameter which is filled with particulate alumina (adjacent to the porous refractory (5)). The particulate alumina functions as the filter (6) to remove dust in the recovered carrier gas. The gas blowing tube (1) penetrates the filter (6) and the porous refractory (5) so that its open end is positioned in the molten steel (75). The open end of the gas recovery tube (2) is plunged into the upper layer of the filter (6) so that it recovers the carrier gas which has passed through the porous refractory (5) and the filter (6).

At the base of the holder (3), the gas blowing tube (1) and the gas recovery tube (2) are connected by connectors (not shown) to the gas circulating circuit (50) mentioned later. These connectors permit tile gas supply-recover probe (70) to be detached easily for disposal after use.

Figure 5:
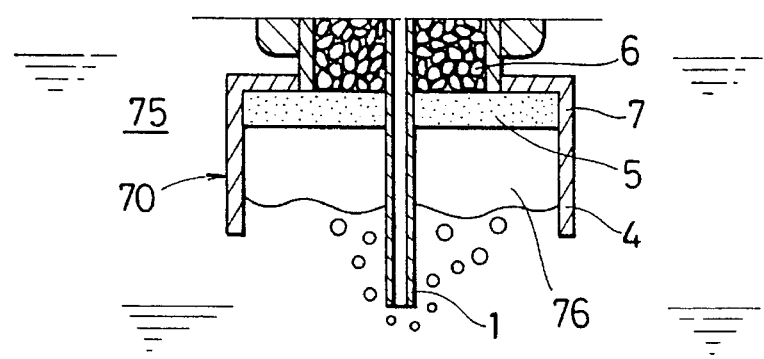
FIG. 5 is a sectional view showing important parts of the gas supply-recover probe having a gas reservoir in the skirt.

The porous refractory (5) passes the carrier gas alone but blocks the molten steel; however, it permits suboxides (such as FeO and MnO) to deposit thereon if the concentration of oxygen is high in molten steel. These suboxides clog the porous refractory (5) due to corrosion. To cope with this situation, it is necessary to adequately control the amount of gas supply and the amount of gas recovery so that the gas reservoir (76) is formed in the skirt (4) which separates the porous refractory (5) from the molten steel (75), as shown in FIG. 5.

The gas supply-recover probe constructed as mentioned above is connected to the unit which is intended to analyze the recovered gas. This unit is made up of the gas circulating circuit (50) and gas branch circuit (51), an embodiment of which is shown in FIG. 3.

The gas circulating circuit (50) consists of a pump (10), a flow meter (11), a valve (12), a pressure gauge (13), a pressure gauge (14), an $H_2O$ filter (15), a switching valve (16), a bypass (17), a switching valve (18), a valve (19), and an infrared gas analyzer (20) for determination of the concentration of oxygen. They are sequentially arranged in the direction of flow of the carrier gas. The valves (12, 19) are connected to each other by a tube which branches off at its middle for connection to an argon cylinder (30), a nitrogen cylinder (31), and a helium cylinder (32), through a flow control valve (27), a pressure gauge (28), and a mixer (29). The valves (12, 19) permit the switching of the gas flow.

Parallel to the bypass (17) is arranged the unit to determine the concentration of nitrogen (62) which consists of an oxidizing furnace (21), a $CO_2$ filter (22), and a thermal conductivity detector (TCD) (23). Either of the bypass (17) and the unit (62) can be selected as the passage of the carrier gas by means of the switching valves (16, 18). The passage from the pump (10) to the flow meter (11) is connected to the branching circuit (51), which constitutes the unit to determine the concentration of hydrogen (63) consisting of a flow control valve (24), an $H_2O$ filter (25), and a semiconductor gas sensor (26). Incidentally, the switching valves (16, 18)

are indicated by a simplified symbol to signify their function.

The gas circulating circuit (50) is provided with the $H_2O$ filter (15) so that the recovered carrier gas passes through it immediately after recovery. The $H_2O$ filter (15) removes water which causes errors when the infrared gas analyzer determines the concentrations of carbon monoxide and carbon dioxide.

The unit to determine the concentration of carbon oxides (61) is in fact the infrared gas analyzer (20). The reason for this is that the analyzer is compact in size and is capable of rapid and accurate analysis. In the case where the infrared analyzer (20) is used to determine the concentration of carbon oxides, the carrier gas is argon.

The unit to determine the concentration of nitrogen (62) is in fact the thermal conductivity detector (23). The reason for this is that the thermal conductor detector is the only apparatus capable of accurate analysis of nitrogen which is too stable to be analyzed by any other means.

For the thermal conductivity detector to be used for accurate analysis, it is desirable that there be a large difference in thermal conductivity between the element to be analyzed and the carrier gas. For the determination of nitrogen, it is necessary to use helium as the carrier gas because helium greatly differs from nitrogen in thermal conductivity. There may be an instance where it takes a long time before the results of determination become available because nitrogen is slower than hydrogen and carbon monoxide in diffusion into the carrier gas and an equilibrium is not reached soon after ten-odd times of circulation through the gas circulating circuit (50). In order to avoid such inconvenience, this embodiment is designed such that the approximate equilibrium value is predicted from the rising curve of the nitrogen concentration determined in the initial stage of determination and nitrogen is compulsorily added to the carrier gas from the nitrogen cylinder (31) by controlling the gas mixer (29) according to the predicted value, so that an equilibrium is reached as soon as possible. The oxidizing furnace (21) oxidizes carbon monoxide in the carrier gas into carbon dioxide, which is subsequently removed by the $CO_2$ filter (22). The reason for this is that carbon monoxide causes errors in determination of the concentration of nitrogen because it has a thermal conductivity which is very close to that of nitrogen.

The fact that the unit to determine the concentration of hydrogen (63) is built into the gas branched circuit (51) in place of the passage of the gas circulating circuit (50) is because hydrogen diffuses rapidly and hence does not need repeated circulation through the gas circulating circuit (50) and because a large amount of oxygen is supplied to the surface of the semiconductor gas sensor (26) prior to determination and hence the carrier gas after determination cannot be returned to the gas circulating circuit (50). Incidentally, in the case where the semiconductor gas sensor is used to determine the concentration of hydrogen, it is necessary to use argon or nitrogen as the carrier gas (although it is possible to use helium as the carrier gas, helium is economically disadvantageous).

Figure 8:
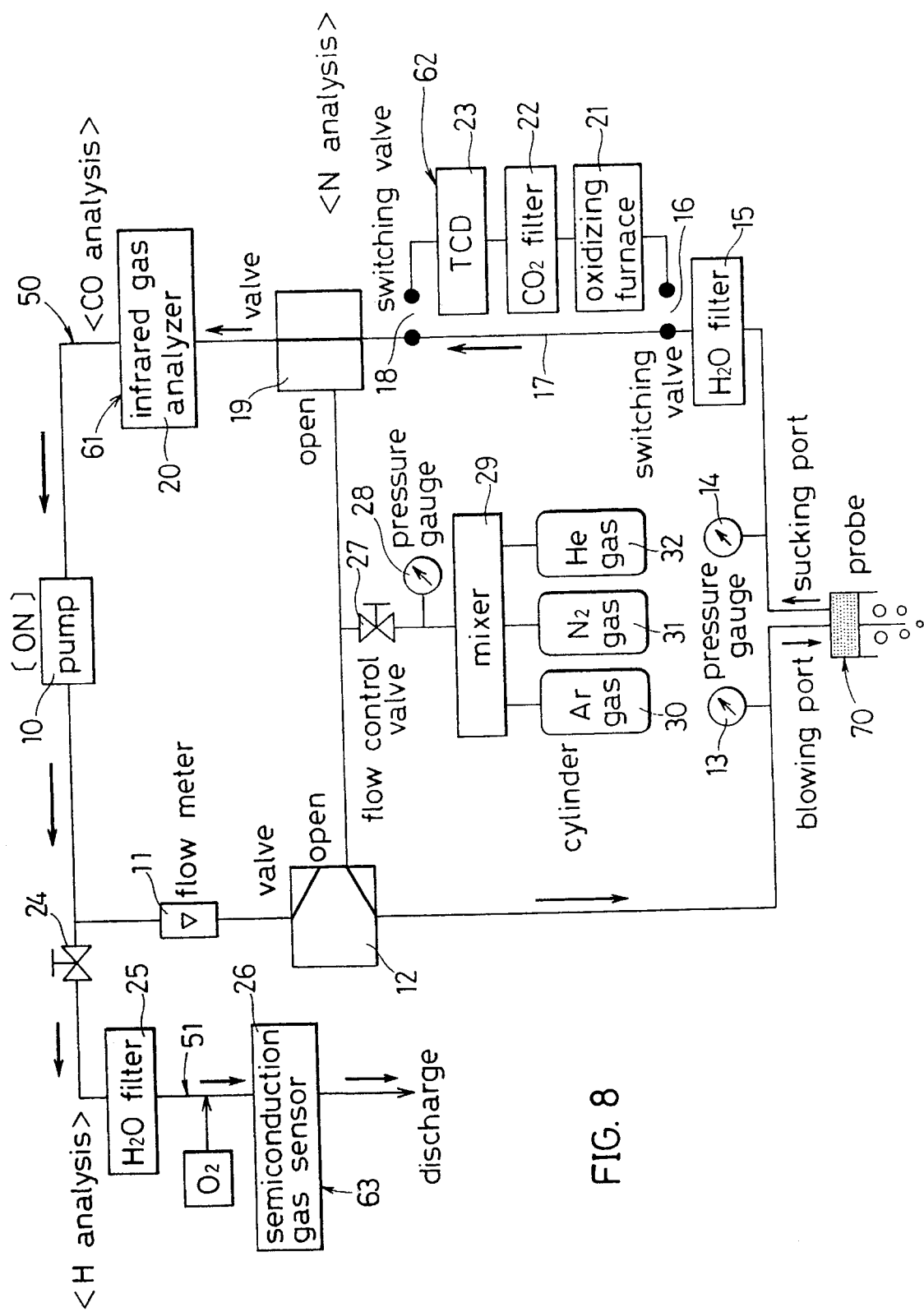
FIG. 8 is a schematic diagram showing the passage through which the carrier gas flows when the concentration of hydrogen is determined.
Figure 9:
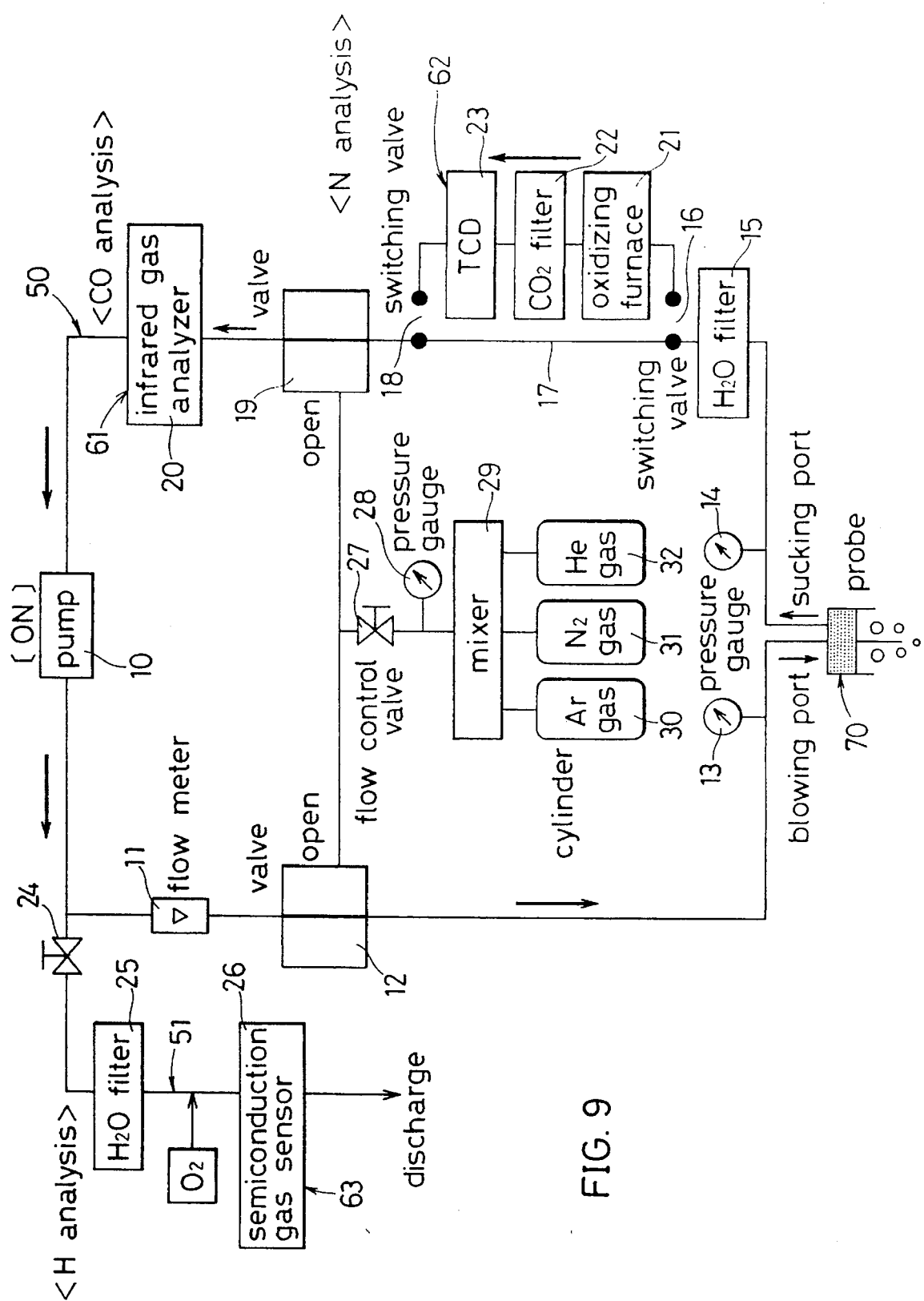
FIG. 9 is a schematic diagram showing the passage through which the carrier gas flows when the concentration of nitrogen is determined.
Figure 10:
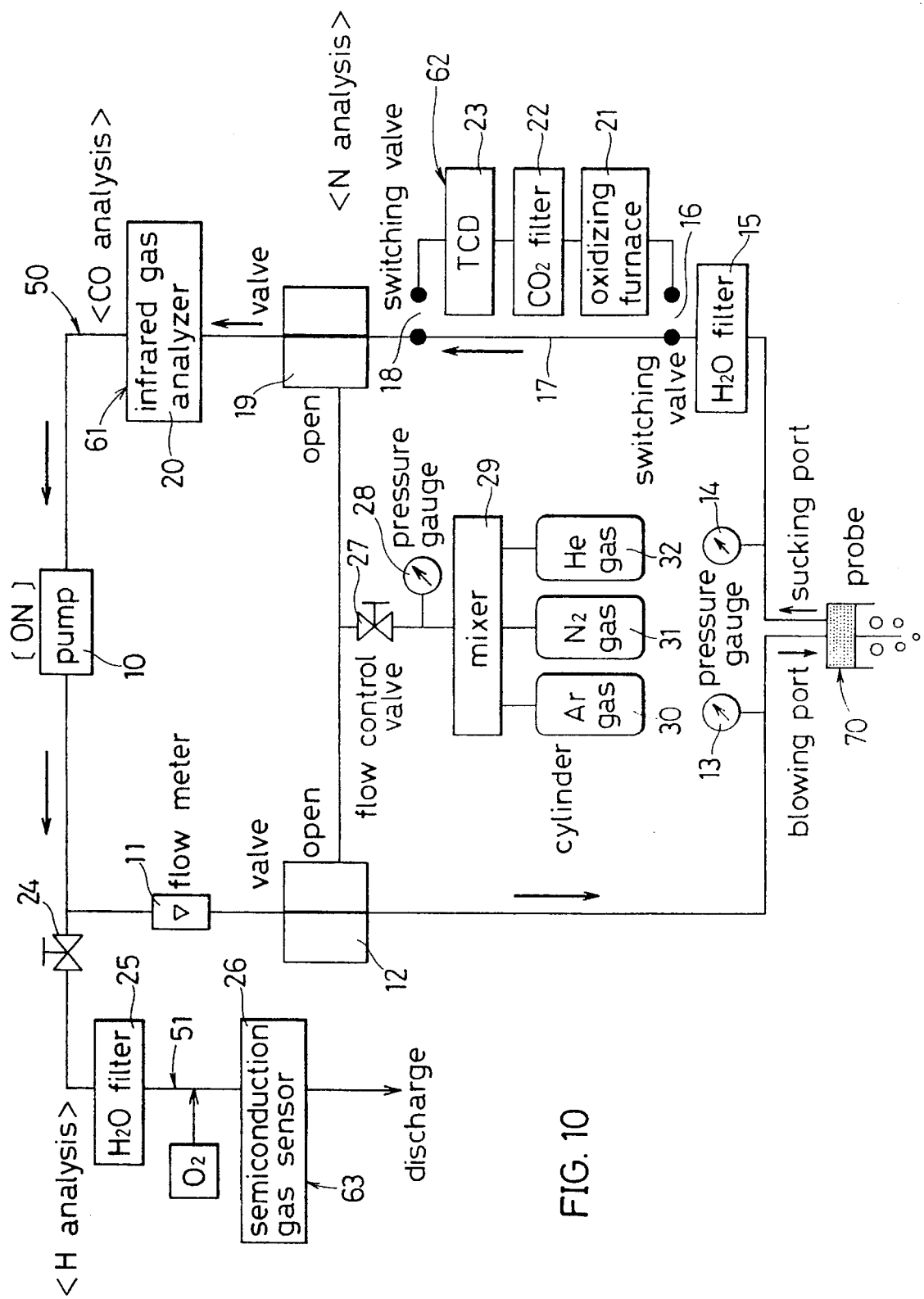
FIG. 10 is a schematic diagram showing the passage through which the carrier gas flows when the concentration of carbon oxides is determined.

The apparatus for sequential and continuous determination constructed as mentioned above is operated in the following manner by switching sequentially the unit to determine the concentration of hydrogen (63), the unit to determine the concentration of nitrogen (62), and the unit to determine the concentration of carbon oxides (61), as illustrated in FIGS. 8 to 10. In an actual steel making mill, it is necessary to determine hydrogen and nitrogen continuously or to determine carbon and nitrogen continuously. In general, molten steel which needs the determination of hydrogen concentration has a low oxygen concentration and molten steel which needs the determination of carbon concentration has a high oxygen concentration. Thus, species of molten steel differ in concentrations of elements to be determined.

In the case where the concentration of hydrogen is to be determined, helium (as the carrier gas) is supplied to the gas circulating circuit (50) from the helium gas cylinder (32) and the carrier gas is introduced to the gas supply-recover probe (70) through the gas circulating circuit (50). Then the carrier gas is blown into molten steel for bubbling through the gas blowing tube (1). The carrier gas which has passed through molten steel is recovered into the gas circulating circuit (50) through the gas recovery tube (2). The recovered carrier gas is introduced to the gas branch circuit (51) through the bypass (17) and the pump (10) without being returned to the gas circulating circuit (50). In the gas branch circuit (51), it is exposed to an oxidizing gas and the concentration of hydrogen is determined by the semiconductor gas sensor (26). The carrier gas is finally discharged from the gas branch circuit (51). During this process, the infrared gas analyzer (20) should be kept off because is gives a meaningless reading when the carrier gas passes through it.

In the case where the concentration of nitrogen is to be determined, the switching valves (16, 18) are directed such that the carrier gas which has passed through the $H_2O$ filter (15) is diverted to the unit to determine the concentration of nitrogen (62), as shown in FIG. 9. The flow control valve (24) is closed to isolate the gas branch circuit (51). With the apparatus arranged as mentioned above, helium (as the carrier gas) is supplied to the gas supply-recover probe (70) from the helium gas cylinder (32). The carrier gas is allowed to bubble in molten steel and then recovered. The recovered carrier gas passes through the unit to determine the concentration of nitrogen (62) and the gas circulating circuit (50) and enters molten steel again. This cycle is repeated several times until the concentration of nitrogen in the carrier gas reaches an equilibrium. An equilibrium is found by continuously monitoring the reading of the thermal conductivity detector (23). In order to expedite the diffusion of nitrogen, a proper amount of nitrogen may be added to the carrier gas from the nitrogen gas cylinder (31). After determination, the carrier gas is discharged from the gas circulating circuit (50) so that the apparatus is ready for subsequent determination.

In the case where the concentrations of carbon monoxide and carbon dioxide are to be determined, the switching valves (16, 18) are directed such that the unit to determine the concentration of nitrogen (62) is separated from the gas circulating circuit (50) and the carrier gas passes through the bypass (17), as shown in FIG. 10. With the apparatus arranged as mentioned above, a prescribed amount of argon is supplied to the gas supply-recover probe (70) from the argon gas cylinder (30). The carrier gas is blown into molten steel for bubbling through the gas blowing tube (1) of the gas supply-recover probe (70). The bubbling promotes the reaction of carbon and oxygen in molten steel to give carbon monoxide and carbon dioxide. The carrier gas containing carbon monoxide and carbon dioxide is recovered by the carrier gas recovery tube (2) and then analyzed by the infrared gas analyzer (20). The recovered carrier gas is blown into molten steel and recovered and passed through the infrared gas analyzer (20) and the gas circulating circuit (50) repeatedly until the concentration of nitrogen in the carrier gas reaches an equilibrium. After circulation through the gas circulating circuit (50) has been carried out as many times as required or for a prescribed period of time, the peak values of carbon monoxide and carbon dioxide are read in the infrared gas analyzer (20). On the basis of these values, the concentration of carbon oxides in molten steel is determined. In this way it is possible to determine the concentration of carbon in molten steel to a precision of the order of ppm.

The gas circulation is repeated as many times as required or for a prescribed period of time in order to bring the concentration of carbon oxides in the carrier gas to an equilibrium and thereby to improve the accuracy of determination. It may be possible to produce the same effect by extending the depth of gas blowing and circulating the gas only once instead of repeating the gas circulation. However, this is not desirable because of the necessity for large-sized equipment. The number of cycles or the length of time for circulation is limited in order to accomplish determination rapidly. Although the repeated gas circulation increases the concentration of carbon oxides, the rate of increase is within a certain limit for the same measuring apparatus. Therefore, if a relationship is established between the concentration of carbon oxides determined after circulation as many times as required or for a prescribed period of time and the concentration of carbon in molten steel, it is possible to accurately determine the concentration of carbon in molten steel by utilizing this relationship. This has been proven. The actual number of cycles for gas circulation depends on the conditions under which determination is carried out. The present inventors' investigation indicates that accurate determination (to a precision of the order of ppm) is possible for the carbon concentration after 300 cc of argon is circulated 10 times. The time required for this determination is about 30 seconds. In other words, this rapidity permits practically real-time determination of the carbon concentration in molten steel which varies from time to time. The carbon concentration determined in this way can be used for feedback control of a refinery.

The concentration of carbon oxides obtained from the infrared gas analyzer (20) is used to estimate the concentration of carbon in molten steel. This estimation is performed with reference to the value read in the unit to determine the concentration of oxygen (64) which is composed of an oxygen concentration cell. This unit (64) is separated from the unit to determine the concentration of carbon oxides (61). However, it may be possible to build an oxygen sensor into the gas supply-recover probe (70).

Incidentally, in the case where the concentration of oxygen is high and stable in the equipment as typified by the RH degassing equipment, it is possible to assume that the concentration of oxygen is constant. In this case, it is possible to estimate the concentration of carbon in molten steel directly from the reading in the infrared gas analyzer (20) without determining the concentration of oxygen.

As mentioned above, the carrier gas is switched from one kind to another each time determination is carried out for the concentrations of hydrogen, nitrogen, and carbon. By contrast, it is not necessary to repeat the immersion of the gas supply-recover probe (70) into molten steel unless the species of molten steel changes, but it is only necessary to switch the carrier gas, with the probe kept immersed in molten steel. In this way it is possible to perform continuously the determination of hydrogen concentration and nitrogen concentration or the determination of carbon concentration and nitrogen concentration. In an actual steel making mill, it is not necessary to determine the concentrations of all of carbon, hydrogen, and nitrogen for the same species of molten steel. However, it is possible to determine the concentrations of these three elements continuously and sequentially if proper selections are made for the carrier gas and the means to determine their concentrations according to the actual equipment involved.

In this embodiment, different carrier gases are used alternately for the same species of molten steel when the concentrations of hydrogen and nitrogen or the concentrations of carbon and nitrogen are determined. However, it may be possible to use the same carrier gas if the means to determine the concentrations of different gases is constructed adequately. Moreover, it may also be possible to obviate the necessity of renewing the carrier gas if the procedure and the preliminary procedure for determination are properly modified. In other words, it may be possible to use the same carrier gas at an equilibrium for determination of each element (such as hydrogen and nitrogen) in molten steel. In this case, it is possible to reduce the number of gas cylinders required.

Figure 11:
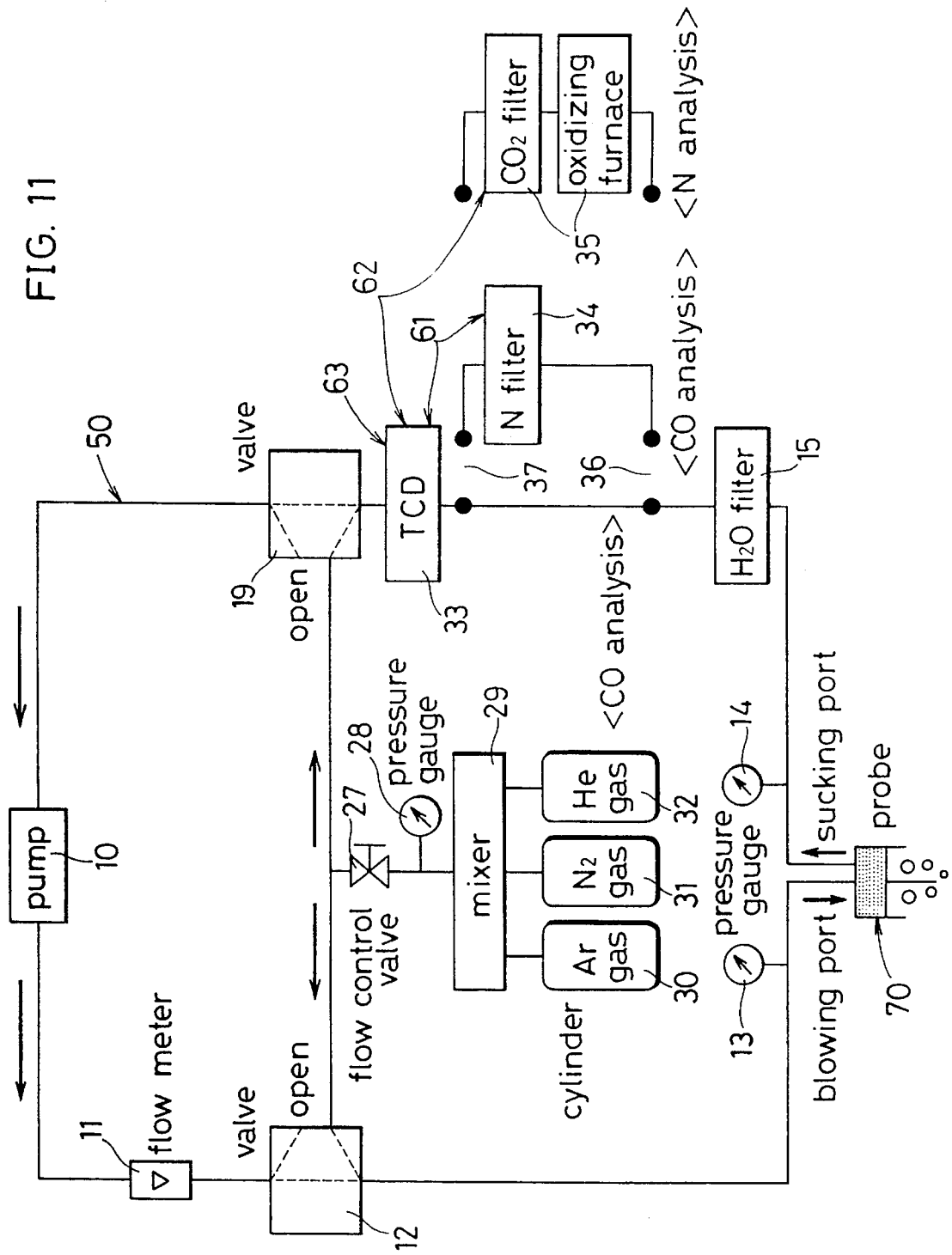
FIG. 11 is a schematic illustration of another embodiment of the apparatus for continuous and sequential determination pertaining to the present invention.

The procedure mentioned above employs the semiconductor gas sensor (26) as the means to determine the concentration of hydrogen, the thermal conductivity detector (23) as the means to determine the concentration of nitrogen, and the infrared gas analyzer (20) as the means to determine the concentration of carbon oxides. The selection of specific units for the determination of specific elements depends on the environment and precision required. An example of such selection is shown in FIG. 11. The gas circulating circuit (50) is provided with the high-precision thermal conductivity detector (33) which is preceded by the bypass (38). Parallel to the bypass (38) are arranged the unit to perform pretreatment for the determination of carbon oxides (34) and the unit to perform pretreatment for the determination of nitrogen (35), either of which can be selected by the switching valves (36, 37).

Figure 6:
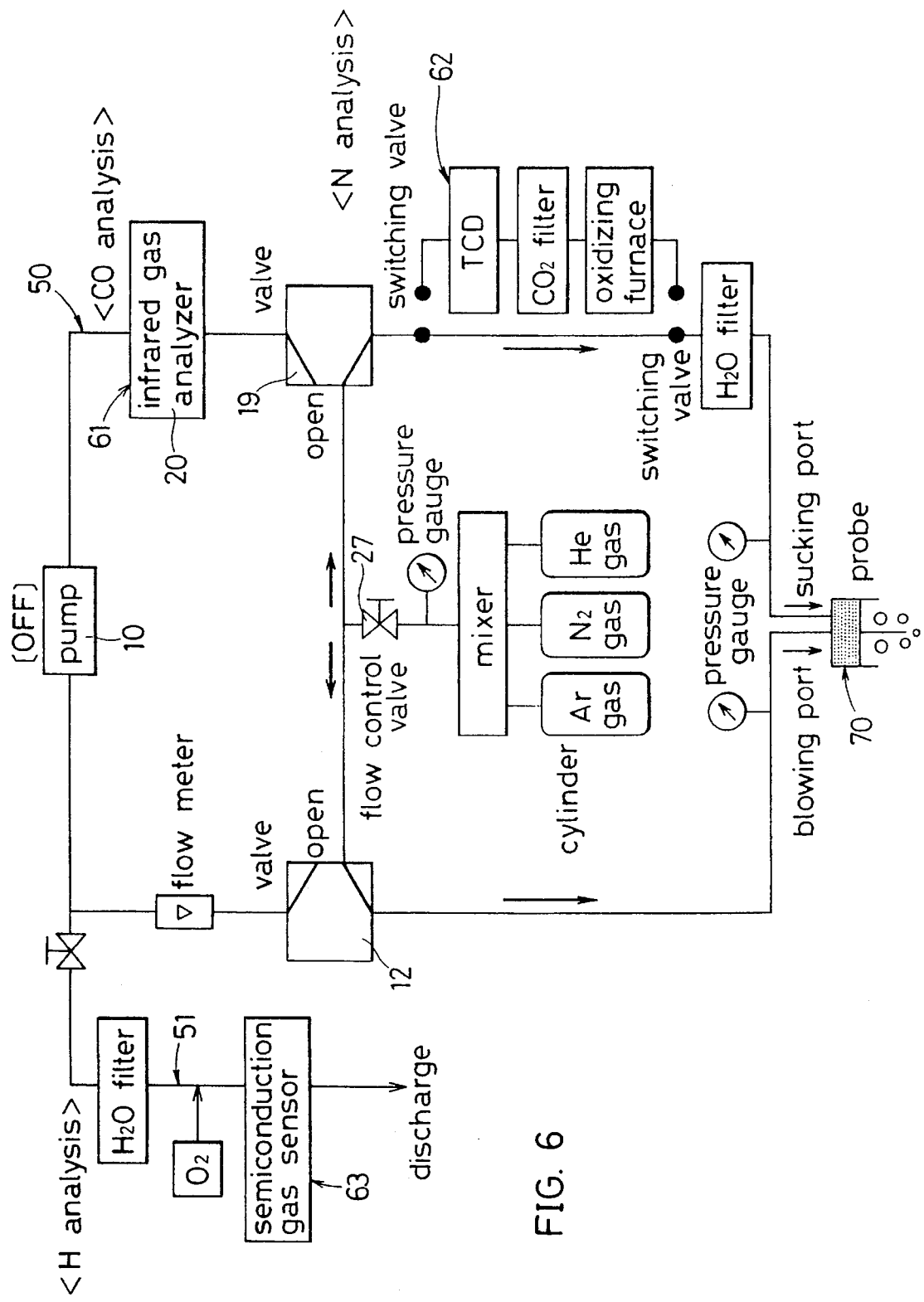
FIG. 6 is a schematic diagram showing how the gas circulating circuit functions.
Figure 7:
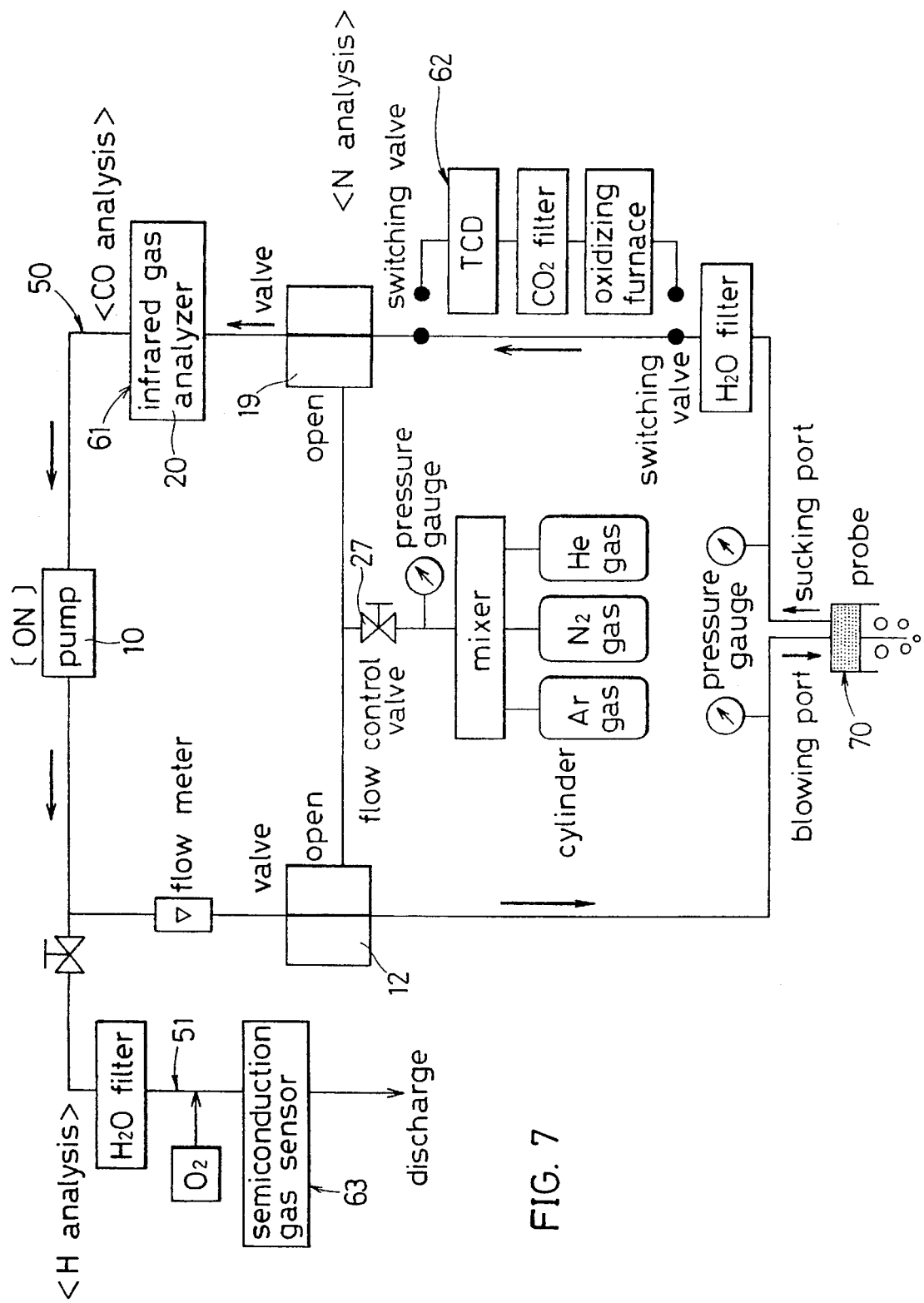
FIG. 7 is a schematic diagram showing how the gas circulating circuit functions.

The gas circulating circuit (50) used in the apparatus of this embodiment functions as mentioned below with reference to FIGS. 6 and 7. The direction of gas flow is indicated by arrows along the gas circulating circuit. The connection of the gas circuit is indicated by solid lines in the valves (12, 19). Whether the pump (10) is turned on or off is indicated by the marking "ON" or "OFF" placed above it.

(1) The apparatus is ready for connection to the gas supply-recover probe (70), with the flow control valve (27) closed and the pump (10) turned off.

(2) The pump (10) is turned on to evacuate air from the piping through the blowing port. The carrier gas delivered from the gas cylinder is discharged through the blowing port.

(3) With the pump (10) turned on or off, the gas supply-recover probe (70) is mounted. In the case where the open end of the blowing tube of the probe (70) is plugged with a low-melting material, the mounting of the probe (70) is recognized by the pressure increase by the pump (10). The blowing port is switched to the carrier gas circuit. In the case where the open end of the blowing tube is not plugged, the pump (10) is immediately turned off for switching to the carrier gas circuit, and the probe (70) is immersed.

(4) As the gas supply-recover probe (70) is immersed to a prescribed depth in molten steel, the end of the blowing tube opens because the low-melting material is melted by the heat of molten steel. Thus the carrier gas is blown into molten steel. The immersion of the probe is recognized by the pressure decrease, and the carrier gas is discharged from both the blowing tube and the sucking tube. (FIG. 6)

(5) The pump (10) is set in motion so as to discharge the residual gas from the piping. Now, the apparatus is ready for gas circulation.

(6) The gas cylinder is isolated from the circulating circuit, and the circulation of the carrier gas is started. The determination of the concentration of carbon oxides by the infrared gas analyzer (20) is started. (FIG. 7)

(7) When the determination is completed, the pump (10) is stopped and the probe (70) is withdrawn. The carrier gas is discharged from both the blowing tube and sucking tube for a proper length of time to make the apparatus ready for the subsequent operation.

In this way the carrier gas is circulated through the gas circulating circuit (50) and the concentration of a specific element is determined. The above-mentioned gas circulating circuit (50) is a mere example, and its structure is not specifically limited so long as it permits the circulation of the carrier gas.

Figure 12:
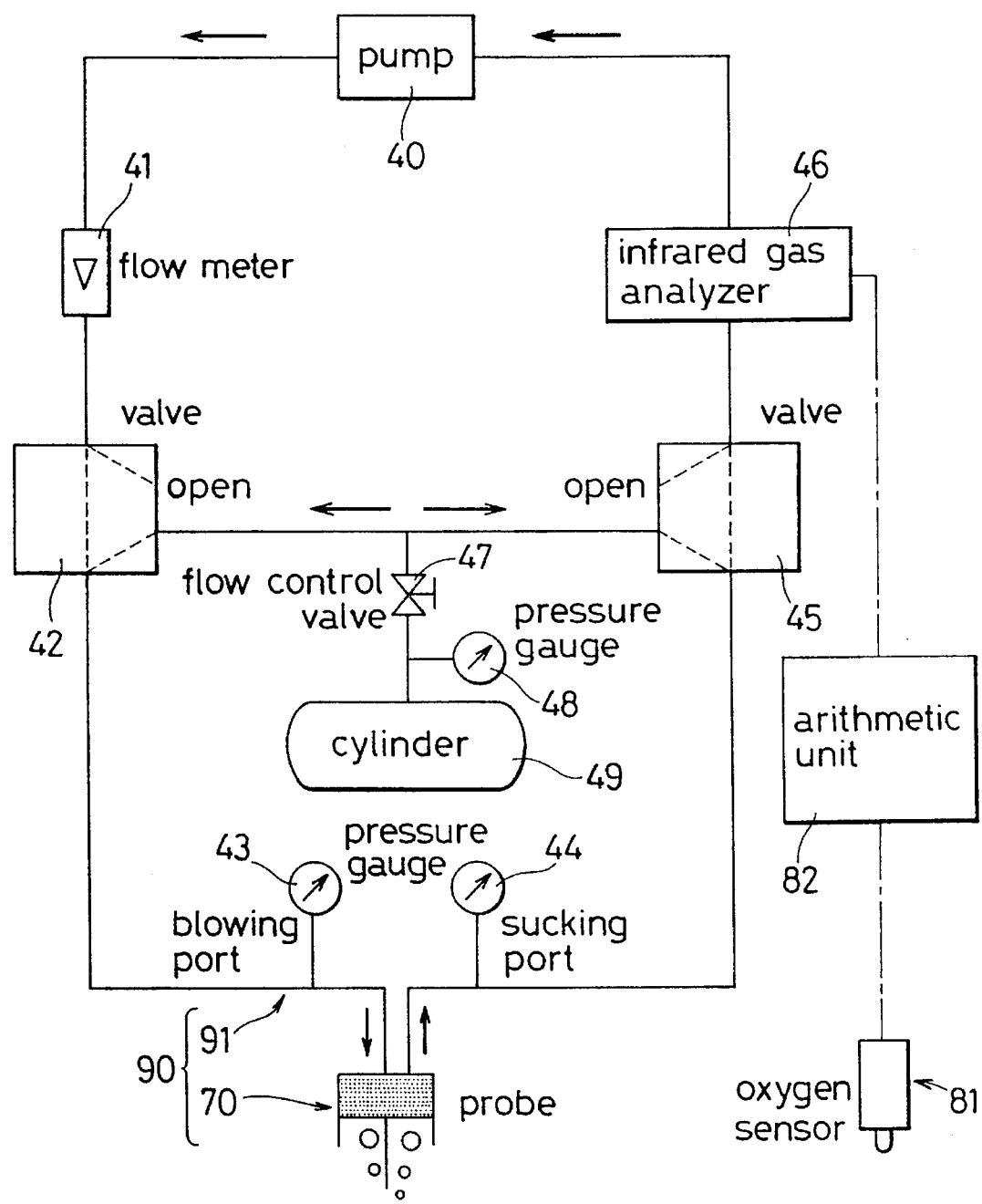
FIG. 12 is a schematic illustration of an embodiment of the apparatus pertaining to the present invention for rapid determination of trace amounts of carbon in molten steel.

The second aspect of the present invention is embodied in an apparatus for rapid determination of trace amounts of carbon in molten steel. This apparatus is explained in the following with reference to FIG. 12. This apparatus is a specialized version of the above-mentioned apparatus for determining three elements continuously and sequentially. The specialization is accomplished by removing the means to determine the concentrations of hydrogen and nitrogen from the above-mentioned apparatus. However, this specialized apparatus has some features in common with the abovementioned apparatus for determining three elements continuously and sequentially. That is, this apparatus is designed such that the carrier gas is bubbled through molten steel, the carrier gas is recovered, the recovered carrier gas is circulated through the gas circulating circuit until an equilibrium is reached between the concentration of the element for analysis in the recovered carrier gas and the concentration of the element for analysis in molten steel, and finally the concentration of the element for analysis in the carrier gas is determined.

This apparatus is composed mainly of the unit to determine the concentration of carbon oxides (90), the unit to determine the concentration of oxygen (81), and the arithmetic unit (82) to calculate the concentration of carbon in molten steel from the values obtained by the two units. In the case where the concentration of oxygen is high and stable in the equipment as typified by the RH degassing equipment, it is possible to assume that the concentration of oxygen is constant. In this case, it is possible to dismount the unit to determine the concentration of oxygen (81) as shown in FIG. 13.

The unit to determine the concentration of oxygen (90) is made up of the gas supply-recover probe (70) to be immersed in molten steel and the gas circulating circuit which constitutes the recovered gas analyzer (91). The gas supply-recover probe (70) is one which was explained above with reference to FIGS. 4 and 5.

Figure 13:
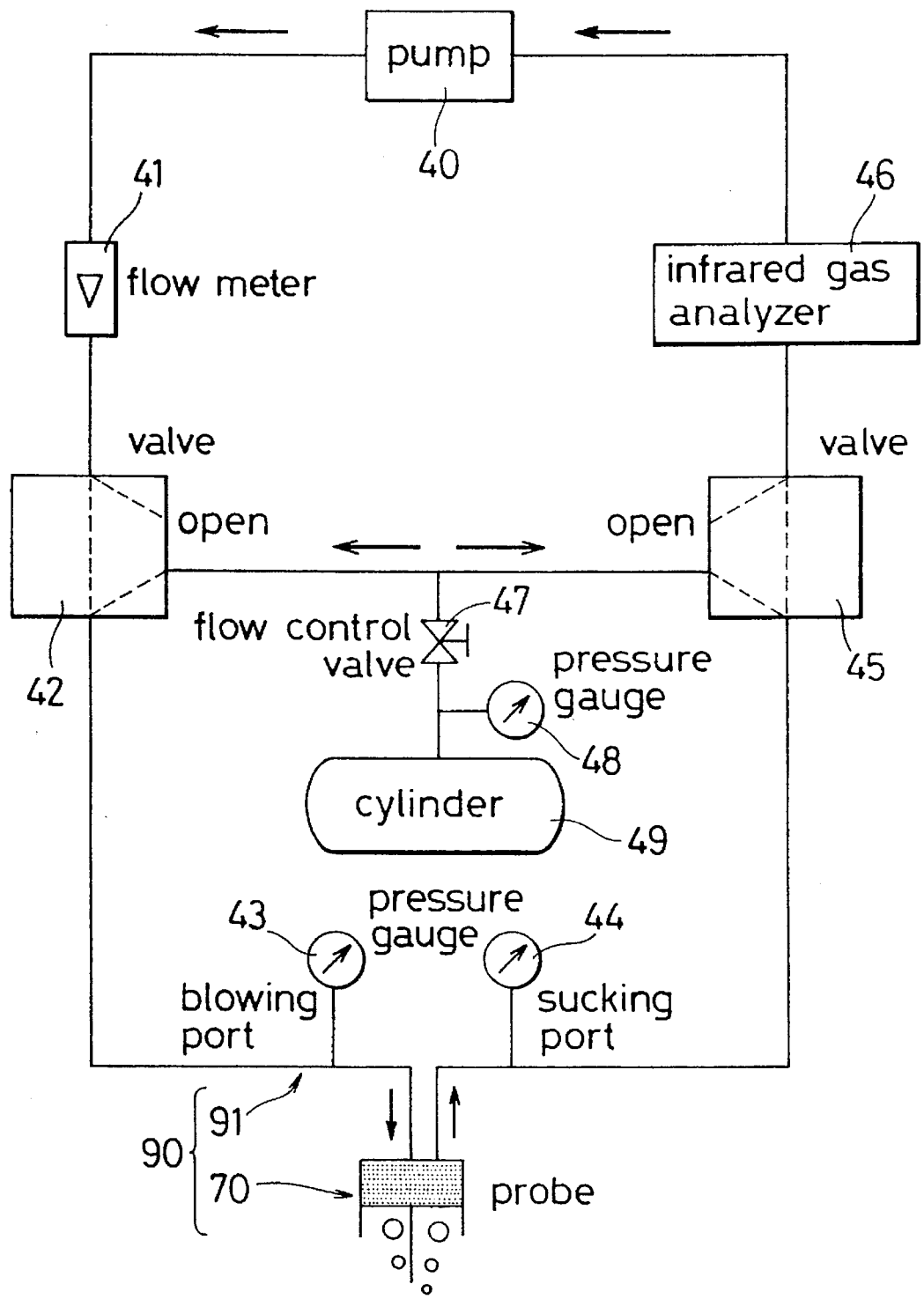
FIG. 13 is a schematic illustration of another embodiment of the apparatus pertaining to the present invention for rapid determination of trace amounts of carbon in molten steel.

The gas supply-recover probe is connected to the gas circulating circuit (91) as shown in FIG. 13.

The gas circulating circuit (91) consists of the pump (40), flow meter (41), valve (42), pressure gauge (43), pressure gauge (44), valve (45), and infrared gas analyzer (46), which are sequentially arranged in the direction of flow of the carrier gas. The valves (42, 45) are connected by a tube which branches off at its middle to the gas cylinder (49), with the flow control valve (47) and the pressure gauge (48) interposed between. The infrared gas analyzer (46) determines the concentrations of carbon monoxide and carbon dioxide; however, it may be replaced by a thermal conductivity detector or semiconductor gas sensor. In this embodiment, the carrier gas supplied from the gas cylinder (49) is argon; however, it may be replaced by any other inert gas.

In the case where a thermal conductivity detector is used as the means to determine the concentration of carbon oxides, it is desirable that the carrier gas greatly differ in thermal conductivity from carbon monoxide and carbon dioxide.

The means to determine the concentration of carbon oxides (90), which is constructed of the gas circulating circuit (91) and the gas supply-recover probe (70) as mentioned above, is operated in the following manner. First, the carrier gas in a proper amount is supplied from the gas cylinder (49). The carrier gas is bubbled in molten steel through the gas blowing tube (1) of the gas supply-recover probe (70). Bubbling promotes the reaction of carbon and oxygen in molten steel which gives rise to carbon monoxide and carbon dioxide. The carrier gas is recovered, together with carbon monoxide and carbon dioxide, by the gas recover tube (2), and the recovered carrier gas is analyzed by the infrared gas analyzer (46). The recovered gas is circulated as many times as required or for a prescribed period of time, and the concentration of carbon oxides in the carrier gas is determined. The thus obtained value is used to estimate to a precision of the order of ppm the concentration of carbon in molten steel. The object of repeating the gas circulation as many times as required or for a prescribed period of time is to increase the concentration of carbon oxides in the carrier gas to an equilibrium, thereby to improve the precision of determination. It may be possible to produce the same effect by extending the depth of gas blowing and circulating the gas only once instead of repeating the gas circulation. However, this is not desirable because of the necessity for large-sized equipment. The number of cycles or the length of time for circulation is limited in order to accomplish determination rapidly. Although the repeated gas circulation increases the concentration of carbon oxides, the rate of increase is within a certain limit for the same measuring apparatus. Therefore, if a relationship is established between the concentration of carbon oxides determined after circulation as many times as required or for a prescribed period of time and the concentration of carbon in molten steel, it is possible to accurately determine the concentration of carbon in molten steel by utilizing this relationship. This has been proven. The actual number of cycles for gas circulation depends on the conditions under which determination is carried out. The present inventors' investigation indicates that accurate determination (to a precision of the order of ppm) is possible for the carbon concentration after 300 cc of argon is circulated 10 times. The time required for this determination is about 30 seconds. In other words, this rapidity permits practically real-time determination of the carbon concentration in molten steel which varies from time to time. The carbon concentration determined in this way can be used for feedback control of a refinery.

The concentration of carbon oxides obtained from the infrared gas analyzer (46) is used to estimate the concentration of carbon in molten steel. This estimation is performed with reference to the value read in the unit to determine the concentration of oxygen (81) which is composed of an oxygen concentration cell. This unit (81) is separate from the unit to determine the concentration of carbon oxides (90). However, it may be possible to build an oxygen sensor into the gas supply-recover probe (70).

Incidentally, in the case where the concentration of oxygen is high and stable in the equipment as typified by the RH degassing equipment, it is possible to assume that the concentration of oxygen is constant. In this case, it is possible to estimate the concentration of carbon in molten steel directly from the reading in the infrared gas analyzer (46) without determining the concentration of oxygen.

Figure 14:
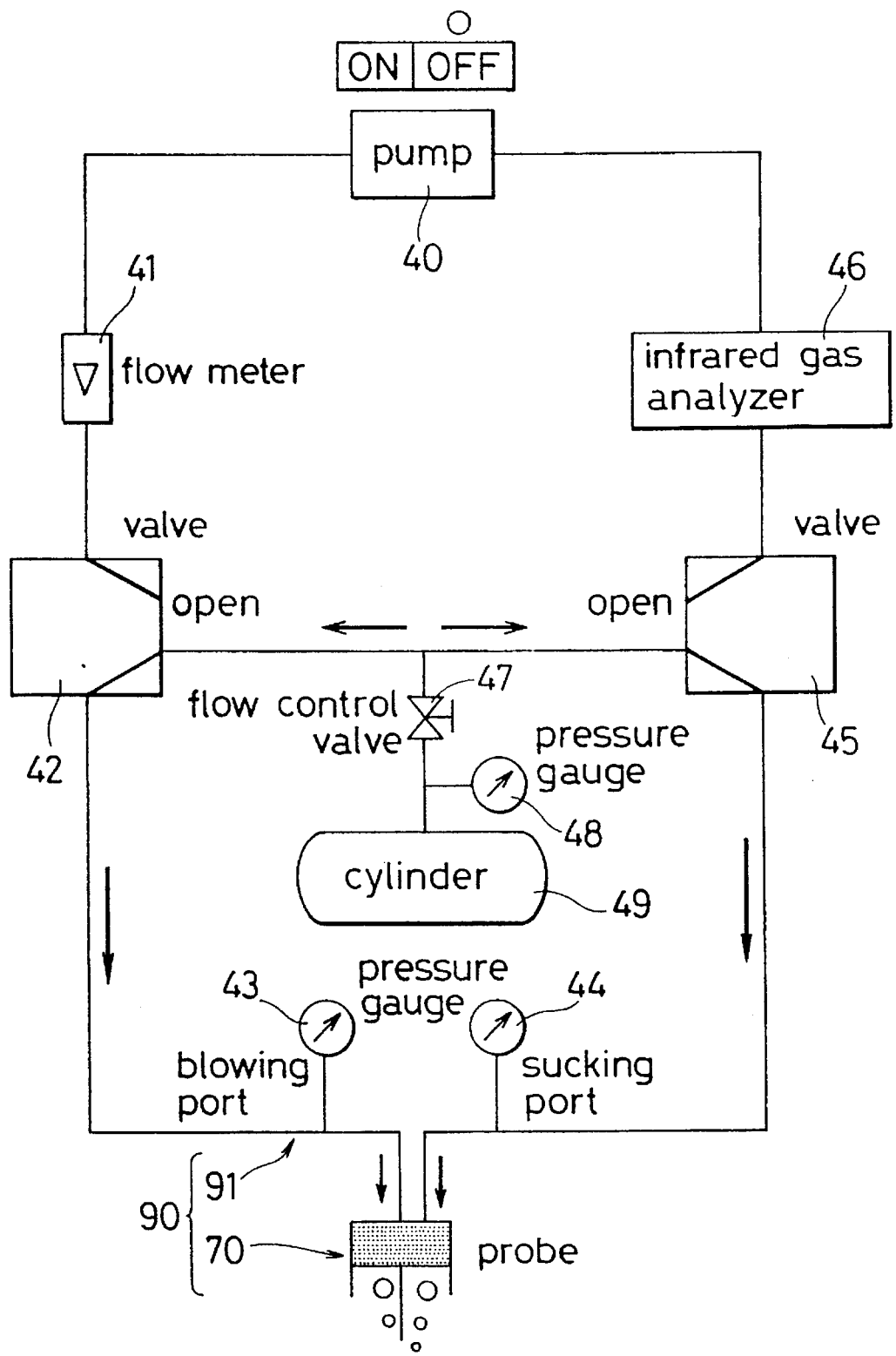
FIG. 14 is a schematic illustration showing how the apparatus for determining the concentration of carbon oxides functions.
Figure 15:
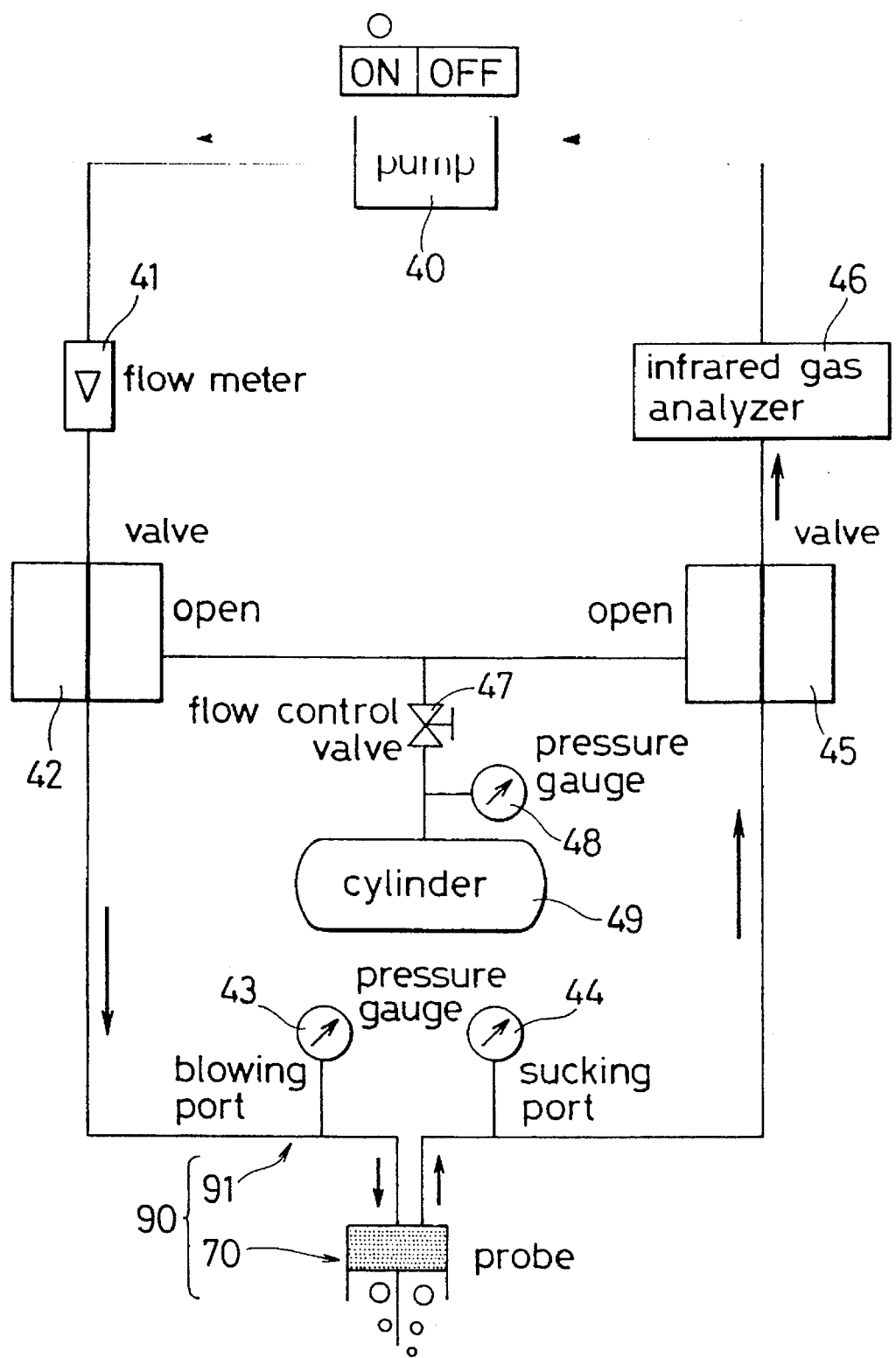
FIG. 15 is a schematic diagram showing how the apparatus for determining the concentration of carbon oxides functions.
Figure 16:
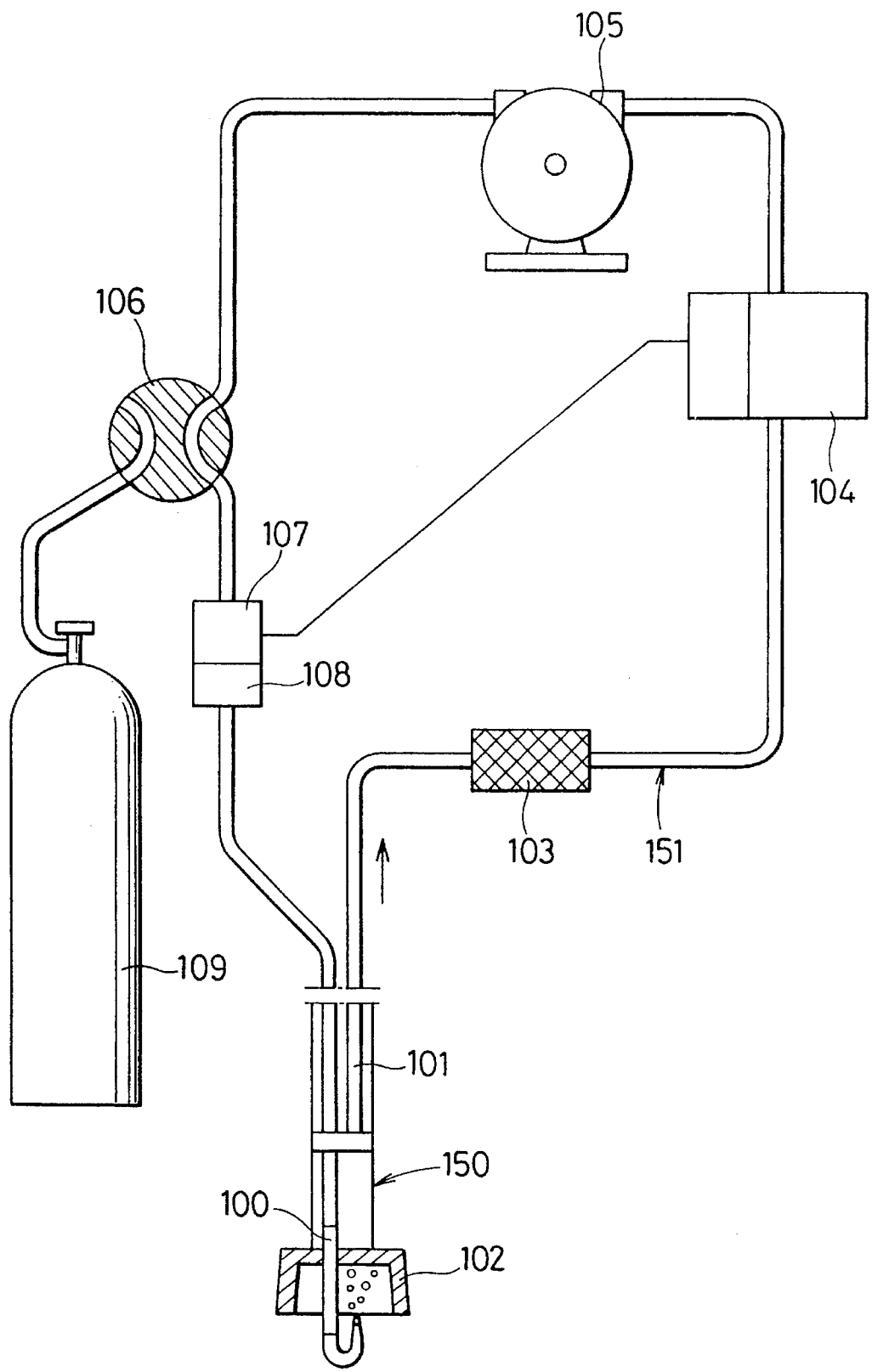
FIG. 16 is a schematic illustration of the conventional apparatus for determining the concentration of hydrogen which is disclosed in Japanese Patent Kohyo No. 502776/1989.

The unit to determine the concentration of carbon oxides (90) functions as mentioned below with reference to FIGS. 14 and 15. The direction of gas flow is indicated by arrows along the gas circulating circuit. The connection of the gas circuit is indicated by solid lines in the valves (42, 45). Whether the pump (40) is turned on or off is indicated by the marking "ON" or "OFF" placed above it.

(1) The apparatus is ready for connection to the gas supply-recover probe (70), with the flow control valve (47) closed and the pump (40) turned off.

(2) The pump (40) is turned on to evacuate air from the piping through the blowing port. The carrier gas delivered from the gas cylinder (49) is discharged through the blowing port.

(3) With the pump (40) turned on or off, the gas supply-recover probe (70) is mounted. In the case where the open end of the blowing tube of the probe (70) is plugged with a low-melting material, the mounting of the probe (70) is recognized by the pressure increase by the pump (40). The blowing port is switched to the carrier gas circuit. In the case where the open end of the blowing tube is not plugged, the pump (40) is immediately turned off for switching to the carrier gas circuit, and the probe (70) is immersed.

(4) As the gas supply-recover probe (70) is immersed to a prescribed depth in molten steel, the end of the blowing tube opens because the low-melting material is melted by the heat of molten steel. Thus the carrier gas is blown into molten steel. The immersion of the probe is recognized by the pressure decrease, and the carrier gas is discharged from both the blowing tube and the sucking tube. (FIG. 14)

(5) The pump (40) is set in motion so as to discharge the residual gas from the piping. Now, the apparatus is ready for gas circulation.

(6) The gas cylinder (49) is isolated from the circulating circuit, and the circulation of the carrier gas is started. The determination of the concentration of carbon oxides by the infrared gas analyzer (46) is started. (FIG. 15)

(7) When the determination is completed, the pump (40) is stopped and the probe (70) is withdrawn. The carrier gas is discharged from both the blowing tube and sucking tube for a proper length of time to make the apparatus ready for the subsequent operation.

In this way it is possible to rapidly determine (in almost real-time manner) the concentration of carbon in molten steel with no deoxidation or slight deoxidation which changes from time to time. The above-mentioned gas circulating circuit (91) is a mere example, and its structure is not specifically limited so long as it permits the circulation of the carrier gas.

[Effect of the invention]

The first aspect of the present invention is embodied in a method and apparatus for sequentially and continuously determining the concentrations of carbon, hydrogen, and nitrogen in molten steel by selecting a carrier gas according to the element to be determined, blowing and bubbling the carrier gas through molten steel through a single gas supply-recover probe which is used in common for all the elements to be determined, recovering the carrier gas from molten steel after bubbling, passing or circulating the recovered carrier gas through a single gas circulating unit which is used in common for all the elements to be determined, determining the concentration of typical elements such as carbon, hydrogen, and nitrogen during the passing or circulation, renewing the carrier gas upon completion of determination of the concentration of a specific element to be analyzed, and repeating the above-mentioned procedure to determine the concentration of another specific element. This constitution makes it possible to continuously determine to a high precision the concentrations of typical elements such as carbon, hydrogen, and nitrogen without the necessity of replacing the instrument for determination. Moreover, since the major units such as the gas supply-recover probe and gas circulating circuit can be used in common for all the elements to be determined, it is not necessary to install a new apparatus for determination. This saves the total cost of the apparatus and facilities the maintenance of the apparatus.

According to the present invention, the bubbling stirs molten steel to react trace amounts of carbon with oxygen in molten steel to give carbon monoxide and carbon dioxide. The determination of these compounds makes it possible to estimate the concentration of carbon in molten steel. This procedure makes it possible to determine an extremely small amount of carbon in molten steel which could not be determined by the conventional procedure. The determination according to the present invention can be carried out so rapidly that it permits one to know (in almost real-time manner) the concentration of carbon in molten steel which changes from time to time. The results of determination can be used for feed-back control of a refinery.

In the case where the concentration of oxygen in molten steel is known and it is not necessary to determine the concentration of oxygen, the apparatus may be simplified and the time required for determination may be shortened.

In determination of nitrogen (which is slow in diffusion), it is desirable to predict the average equilibrium value of nitrogen concentration from the rising curve of the nitrogen concentration obtained in the initial stage of determination and to add nitrogen compulsorily from a nitrogen cylinder according to the predicted value so as to establish an equilibrium as soon as possible. This procedure permits one to determine the concentration of nitrogen extremely rapidly.

The second aspect of the present invention is embodied in a method and apparatus for rapidly determining trace amounts of carbon in molten steel with no deoxidation or slight deoxidation, by bubbling a carrier gas through molten steel, thereby stirring molten steel and reacting trace amounts of carbon with oxygen in molten steel to give carbon monoxide and carbon dioxide, determining the concentrations of the carbon monoxide and carbon dioxide, and estimating the concentration of carbon in molten steel from the results of such determination. This procedure makes it possible to determine an extremely small amount of carbon in molten steel which could not be determined by the conventional procedure, as in the case of the method and apparatus (pertaining to the first aspect of the present invention) for determining the concentrations of carbon, hydrogen, and nitrogen in molten steel sequentially and continuously.

What is claimed is:

1. A method for determining sequentially and continuously the concentrations of carbon, hydrogen, and nitrogen in molten steel, said method comprising bubbling through molten steel an inert gas as a carrier gas selected according to any specific element to be determined among carbon, hydrogen, and nitrogen in molten steel, recovering the carrier gas containing the specific element through a gas supply-recover probe immersed in molten steel, circulating or passing the recovered carrier gas through a gas circulating circuit, performing the bubbling and recovery of the carrier gas once or several times so that the concentration of the specific element in the carrier gas reaches an approximate or complete equilibrium with the concentration of the specific element in molten steel, determining the concentration of the specific element by means to determine the concentration of one or more specific elements which is installed in said gas circulating circuit or in a gas circuit branching off from said gas circulating circuit, discharging the carrier gas from the gas circulating circuit to complete a series of steps for determining the concentration of the specific element, and repeating said steps with a renewed carrier gas to determine the remaining elements to be determined.

2. An apparatus for determining sequentially and continuously the concentrations of carbon, hydrogen, and nitrogen in molten steel, said apparatus comprising one or more than one source to supply an inert gas as a carrier gas according to the element to be determined; a gas supply-recover probe consisting of a gas blowing tube with an open end and a gas recovery tube to recover the carrier gas through a porous part which is positioned in molten steel above the open end of the gas blowing tube; a gas circulating circuit through which the carrier gas supplied from the carrier gas source is circulated compulsorily by a circulating pump through the gas supply-recover probe as many times as required or for a prescribed period of time; a group of means to determine the concentration of a specific element including means to determine the concentration of carbon oxides, means to determine the concentration of hydrogen, and means to determine the concentration of nitrogen installed in the gas circulating circuit or in a gas circuit branching off from the gas circulating circuit; a means to determine the concentrations of oxygen which is constructed integrally with or separately from the gas supply-recover probe; and an arithmetic unit which receives the data of the concentrations of carbon oxides and oxygen from the means to determine the concentrations of carbon oxides and oxygen and calculates the concentration of carbon in molten steel from such data.

3. An apparatus for sequentially and continuously determining the concentrations of carbon, hydrogen, and nitrogen in molten steel as defined in claim 2, wherein the means to determine the concentration of a specific element is provided with a pretreatment unit to remove harmful components from the carrier gas.

4. An apparatus for sequentially and continuously determining the concentrations of carbon, hydrogen, and nitrogen in molten steel as defined in claim 2 or 3, wherein the means to determine the concentration of carbon oxides is an infrared gas analyzer, the means to determine the concentration of hydrogen is a semiconductor gas sensor, and the means to determine the concentration of nitrogen is a thermal conductivity detector.

5. A method for rapidly determining trace amounts of carbon in molten steel, said method comprising bubbling an inert gas as a carrier gas through molten steel with no deoxidation or slight deoxidation, thereby stirring molten steel and causing carbon and oxygen to react with each other at the interface between bubbles and molten steel to give carbon monoxide and carbon dioxide, recovering the carrier gas together with carbon monoxide and carbon dioxide, circulating or passing the recovered carrier gas through the gas circuit in which is installed a means to determine the concentration of carbon oxides, performing the steps of the bubbling and recovery of the carrier gas once or several times, thereby gradually increasing the concentrations of carbon monoxide and carbon dioxide in the carrier gas until they equilibrate with those of oxygen and carbon in molten steel, determining the concentrations of carbon monoxide and carbon dioxide in the carrier gas by the above-mentioned means to determine the concentrations of carbon oxides after the circulation has been carried out as many times as required or for a prescribed period of time, and estimating the concentration of carbon in molten steel from the relationship between the concentrations of carbon monoxide and carbon dioxide and the concentration of oxygen in molten steel.

6. An apparatus for rapidly determining trace amounts of carbon in molten steel, which comprises a source to supply an inert gas as a carrier gas; a gas supply-recover probe consisting of a gas blowing tube with an open end and a gas recovery tube to recover the carrier gas through a porous part which is positioned in molten steel above the open end of the gas blowing tube; a gas circulating circuit through which the carrier gas supplied from the carrier gas source is circulated compulsorily by a circulating pump through the gas supply-recover probe as many times as required or for a prescribed period of time, said gas circulating circuit being provided therein a means to determine the concentrations of carbon oxides; a means to determine the concentrations of oxygen which is constructed integrally with or separately from the gas supply-recover probe; and an arithmetic unit which receives the data of the concentrations of carbon oxides and oxygen from the means to determine the concentrations of carbon oxides and oxygen and calculates the concentration of carbon in molten steel from such data.

* * * * *